(12) United States Patent
Pauletti et al.

(10) Patent No.: US 8,178,123 B2
(45) Date of Patent: *May 15, 2012

(54) METHOD FOR AUGMENTATION OF INTRAEPITHELIAL AND SYSTEMIC EXPOSURE OF THERAPEUTIC AGENTS HAVING SUBSTRATE ACTIVITY FOR CYTOCHROME P450 ENZYMES AND MEMBRANE EFFLUX SYSTEMS FOLLOWING VAGINAL AND ORAL CAVITY ADMINISTRATION

(75) Inventors: Giovanni M. Pauletti, Loveland, OH (US); Donald C. Harrison, Cincinnati, OH (US); Kishorkumar J. Desai, Westchester, OH (US)

(73) Assignee: Femina Pharma Incorporated, Miami, FL (US)

( * ) Notice: Subject to any disclaimer, the term of this patent is extended or adjusted under 35 U.S.C. 154(b) by 1436 days.

This patent is subject to a terminal disclaimer.

(21) Appl. No.: 11/522,126

(22) Filed: Sep. 15, 2006

(65) Prior Publication Data

US 2007/0036834 A1    Feb. 15, 2007

Related U.S. Application Data

(63) Continuation-in-part of application No. 11/208,209, filed on Aug. 18, 2005, now abandoned, which is a continuation of application No. 10/226,667, filed on Aug. 21, 2002, now Pat. No. 6,982,091.

(60) Provisional application No. 60/717,680, filed on Sep. 15, 2005, provisional application No. 60/315,877, filed on Aug. 29, 2001.

(51) Int. Cl.
*A61F 2/02* (2006.01)
(52) U.S. Cl. .................................................. 424/423
(58) Field of Classification Search .................... None
See application file for complete search history.

(56) References Cited

U.S. PATENT DOCUMENTS 6,905,701 B2 * 6/2005 Pauletti et al. ............. 424/433

* cited by examiner

*Primary Examiner* — Carlos Azpuru
(74) *Attorney, Agent, or Firm* — Antonelli, Terry, Stout & Kraus, LLP.

(57) ABSTRACT

A vaginal or buccal delivery of therapeutic agents having a substrate affinity for metabolic cytochrome P-450 enzymes and membrane efflux transporter systems. A method for augmentation of systemic exposure to the therapeutic agents having a substrate affinity for cytochrome P-450 enzymes and membrane efflux transporter systems, by delivering said agents to the systemic circulation through vaginal or buccal mucosa.

22 Claims, 2 Drawing Sheets

METHOD FOR AUGMENTATION OF INTRAEPITHELIAL AND SYSTEMIC EXPOSURE OF THERAPEUTIC AGENTS HAVING SUBSTRATE ACTIVITY FOR CYTOCHROME P450 ENZYMES AND MEMBRANE EFFLUX SYSTEMS FOLLOWING VAGINAL AND ORAL CAVITY ADMINISTRATION

This application is based on and claims priority of the Provisional application Ser. No. 60/717,680, filed on Sep. 15, 2005 and is a Continuation-in-Part of patent application Ser. No. 11/208,209, filed Aug. 18, 2005, which is a Continuation application of application Ser. No. 10/226,667, filed Aug. 21, 2002, which is based on and claims priority of Provisional application Ser. No. 60/315,877, filed Aug. 29, 2001.

BACKGROUND OF THE INVENTION

1. Field of the Invention

The current invention concerns generally a vaginal or buccal administration of therapeutic agents having a substrate affinity for metabolic cytochrome P-450 enzymes and membrane efflux transporter systems. In particular, the invention concerns a method for augmentation of intraepithelial and/or systemic exposure to the therapeutic agents having a substrate affinity for cytochrome P-450 enzymes and membrane efflux transporter systems, by delivering said agents to the vaginal or oral cavity.

2. Background and Related Disclosures

Cancer and HIV/AIDS viral diseases have become a worldwide problem that needs attention of the medical community.

More than 53 million people worldwide are infected with the HIV/AIDS virus. The dramatically increased incidence of viral infections among women is particularly worrisome because of its risk of infecting unborn children in-utero and consequently posing as one of the major causes for spread of HIV/AIDS.

Cancer has also become one of the leading causes of death worldwide and with decreasing death rates from heart disease in almost all populations it is or will soon become the largest cause of death in the worldwide population.

Facing the increasing risk of spread of the HIV virus, a number of new pharmaceuticals for effective prevention, treatment, control and management of HIV/AIDS has been developed in the past decade. These new pharmaceuticals encompass new drug classes having different biological, physical and/or chemical properties. The new drug classes include, for example and among others, nucleoside analogs, reverse transcriptase inhibitors and HIV protease inhibitors. In many cases, drug cocktails prepared of at least three different drugs of the same or different classes need to be given to a patient to achieve a therapeutic effect. The cost of these treatments is high and exceeds, according to the World Health Organization figures, $3,000 per year/patient.

Similarly, in the past two decades, the major improvement in the treatment of cancer has been achieved with a development of the new cytostatic and/or cytotoxic agents for both the eradication of cancer and/or for inhibiting and limiting its metastatic capabilities. As in a case of the HIV infections, in most cases, a combination of several drugs is administered in order to gain full therapeutic effects.

It has been long known and recognized that systemic exposure of a drug administered via the oral route is quantitatively limited by the intrinsic aqueous solubility, intestinal membrane permeability as well as by hepatic elimination. To improve the efficiency of the drug development and to recommend methods for drug classification according to their bioavailability, various drugs were defined by their aqueous solubility and intestinal membrane permeability using the Biopharmaceutical Classification System (Amidon et al., *Pharm. Res.*, 12: 413-420 (1995)) into four categories designated Class I-IV. Class I drugs have high permeability and high solubility. Class II drugs have high permeability and low solubility. Class III drugs have low permeability and high solubility. Class IV drugs have low permeability and low solubility.

Consequently, the Class I drugs that have both high aqueous solubility and intestinal membrane permeability have also high bioavailability. On the other hand, Classes II-IV have low, often unacceptably low bioavailability depending on the degree of their solubility and/or permeability. The lowest bioavailability have drugs classified in Class IV.

Typically, in a number of drugs classified in the drug classes II-IV, only a minor fraction of the dose administered into the gastrointestinal tract finally reaches the systemic circulation. Pharmacokinetically, this is defined as limited or low oral bioavailability. Such low oral bioavailability is particularly observed for drugs widely used in the treatment of HIV/AIDS and a wide variety of cancers.

Many anti-cancer drugs and HIV therapeutics have the ability to induce molecular regulation mechanisms common to metabolizing enzymes and efflux systems in intestinal cells and the liver that lead to an increased expression of these proteins. As a result, efficacy of drug therapy decreases after some time due to drug-induced efflux activity and metabolic activities. This can lead to greater variability in patient treatment and even to subtherapeutic drug levels, which may enhance development of drug resistance, a phenomenon that is clinically associated with greater therapy failure. The above mentioned drug-induced regulatory pathways are expected to have a minimal impact on systemic drug levels following vaginal and buccal administration due to the intrinsic low expression levels of efflux systems and metabolizing enzymes in these tissues.

Additionally, and directly dependent on their bioavailability, the cost of these drugs, and particularly those needed for drug cocktails used for treatment of HIV/AIDS and cancer, both individually or combinations thereof, are prohibitive. This is particularly true for drugs where a vast quantity of the orally administered drug is either passed through the digestive system without entering the systemic circulation and excreted, or is at least partially metabolized and inactivated by the liver, before the drug gets to its intended target tissue.

Notwithstanding the above, to further complicate the treatments for HIV/AIDS and cancer, many of these drugs are also highly cytotoxic or have other undesirable secondary symptom such as irritating the GI system and therefore their quantity must be limited to minimum in order to prevent undesirable cytotoxic effects on other non-diseased tissues or prevent undesirable secondary symptoms, such as nausea, vomiting or other discomforts of the patients.

Thus it would be desirable to have available system that would augment systemic delivery of these cytotoxic, irritating, low bioavailability and/or expensive drugs and to permit use of lower dosages to obtain the same therapeutic effect.

Attempts have been made previously by inventors to provide an effective method and compositions for delivery of the chemotherapeutic drugs to female patients. Such efforts are described, for example, in the U.S. Pat. No. 6,982,091 issued on Jan. 3, 2006.

The previously disclosed methods provide an excellent means for delivery of drugs classified by BCS in Class I, having high intestinal membrane permeability and aqueous solubility. However, many of the currently used drugs as an anti-viral or anti-cancer treatment have low bioavailability due to their low aqueous solubility and/or low intestinal membrane permeability. Moreover, many of the Class II-IV drugs also show major GI toxicity and low oral absorption and although the vaginal delivery of these drugs described in the above cited patent application have considerably improved these symptoms, there is still a need for further improvements in their absorption and toxicity.

In addition to the therapeutic benefit of greater systemic exposure of anti-cancer and anti-viral drugs following buccal and vaginal administration, the methods described in this invention will also enhance topical treatment of neoplasia or pre-cancerous lesions present in the mucosae accessible via the oral and vaginal cavity. This includes epithelial dysplasia and invasive cancer of the female lower genital tract, such as cervical cancer and vaginal intraepithelial neoplasia, as well as oral squamous cell carcinoma. Epidemiologically, the prevalence of those malignancies correlates with chronic viral infections, particularly with subsets of the human papillomavirus (HPV) and cytomegalovirus (CMV), respectively (Ogura et al., *Pathol. Int.,* 56: 301-308 (2006); Furrer et al., *J. Oral Pathol. Med.,* 35, 338-344 (2006)). Therapeutic efficacy of anti-cancer and anti-viral drugs after oral administration is unsatisfactory in these cases because of limited systemic exposure. However, even after local drug administration, intracellular concentration of the pharmacological agent required for limiting HPV and CMV replication cannot be achieved as a result of highly active membrane efflux systems and metabolizing cytochrome P450 isozymes. Consequently, novel delivery approaches that increase intraepithelial drug concentrations in the infected oral or genital region are required to address this unmet medical need.

It is therefore, a primary object of this invention to provide a method for augmenting drug delivery of anti-viral and/or anti-cancer drugs into epithelial cells and/or into the systemic circulation by delivering such drugs to a subject in need thereof vaginally or buccally in an especially formulated composition increasing their therapeutic efficacy by providing means for increasing the drug solubility and permeability.

All patents, patent applications and publications cited herein are hereby incorporated by reference.

SUMMARY

One aspect of the current invention is vaginal or buccal delivery of therapeutic agents having a substrate affinity for cytochrome P-450 enzymes and membrane efflux transporter systems.

Another aspect of the current invention is a method for augmentation of epithelial concentration and systemic exposure of therapeutic agents having a substrate affinity for cytochrome P-450 enzymes and membrane efflux transporter systems by using a vaginal or buccal drug delivery compositions and/or devices.

Still another aspect of the current invention is a method for augmentation of intraepithelial concentration and/or systemic bioavailability for delivery of anti-viral and/or anti-cancer therapeutic agents having a substrate affinity for cytochrome P-450 enzymes and membrane efflux systems by using a vaginal or buccal drug delivery of these drugs into the systemic circulation by delivering such drug to a subject in need thereof vaginally or buccally in an especially formulated composition increasing the drug's bioavailability by providing means for increasing the drug solubility and permeability through the vaginal or buccal mucosa. In particular, incorporation of non-ionizable glycol ether and/or botanical bioavailability modulators.

DEFINITIONS

Figure 1:
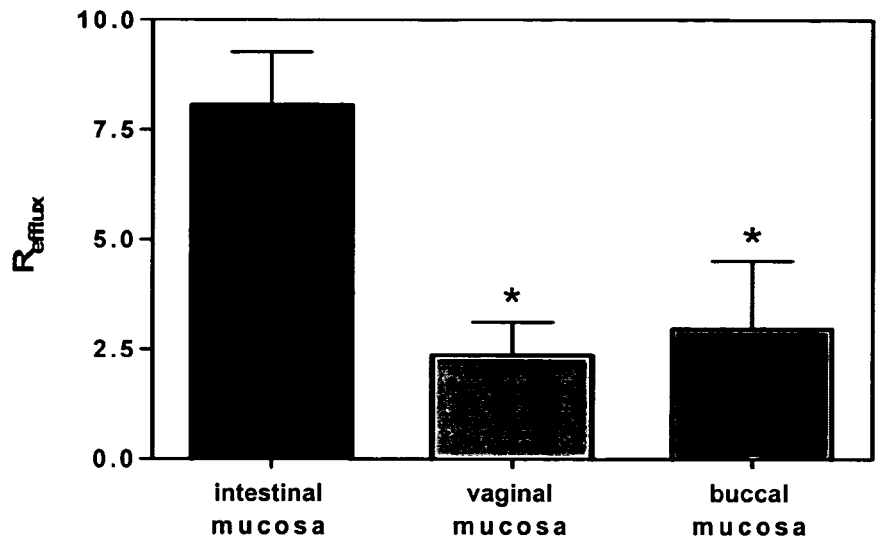
FIG. 1 is a graph that may be obtained illustrating contribution of membrane efflux systems limiting transepithelial transport of ritonavir across intestinal, vaginal and buccal rabbit mucosa in vitro.

As used herein:

"Drug", "pharmaceutical agent", "therapeutical agent", "therapeutically effective agent" or "agent" means a therapeutically effective compound suitable for treatment, management or control of cancer or HIV/AIDS or any other pharmaceutically acceptable and therapeutically active agent or a mixture thereof.

"Chemotherapeutic" means an agent involved in treatment of cancer disease, typically malignancy, by means of a chemical substance or drug that exhibits cytostatic and/or cytotoxic effects on tumor cells.

"Inhibitor of membrane efflux systems" means a chemical compound, which is suitable to partially or completely block the functional activity of membrane efflux transporter systems. Such inhibitor is typically a substrate for membrane transport proteins, such as P-glycoprotein (P-gp) and multidrug-resistance associated protein (MRP), involved in the cellular efflux of drugs.

"MRP" means multidrug-resistance associated protein.

"MDR" means multidrug resistance.

"Continuous delivery" means continuous and uninterrupted release of the drug from the formulation or device and delivering such drug in continuous manner.

"Pulsed delivery" means a release and delivery of the drug in intermittent intervals. Such pulsed delivery may be provided, for example, by formulating the drug in individual layers interspaced with inactive layer of dissolvable coatings or by using different formulating agents.

"Interesterified stone oil" means a vegetable oil ethoxylated by replacing part of glycerol of the glycerides contained in vegetable oil by polyoxyethylene-glycols. Such replacement results in hydrophilic properties. Example of the interesterified stone oil is LABRAFIL®, particularly LABRAFIL®® M 1944 CS, commercially available from Gattefosse, Paramus, N.J.

"Mucosal" or "mucoadhesive" means a composition which is suitable for administration to the mucosal tissue and adheres to such mucosal tissue.

"Sorption promoter", "penetration enhancer", or "permeation enhancer" means a compound which promotes drug penetration of, or permeation through, a mucosal tissue, that is promoting absorption of the drug or compound into the mucosal tissue as well as transporting the drug through the tissue.

"BCS" means a Biopharmaceutical Classification System developed by the Office of Pharmaceutical Science of the U.S. Food and Drug Administration Center for Drug Evaluation and Research.

"Botanical bioavailability modulator" means natural product originating from plant, microbial, and animal sources that modulates functional activity of membrane efflux systems and/or cytochrome P450 isozymes.

DETAILED DISCLOSURE OF THE INVENTION

The current invention concerns generally a method for improved vaginal or buccal delivery of certain therapeutic agents that are therapeutically effective and urgently needed for treatment, control and management of cancer and HIV/AIDS diseases. The therapeutic agents in question are, among others, for example nucleoside analogs, reverse transcriptase inhibitors, HIV protease inhibitors and other compounds having a substrate affinity for drug-metabolizing cytochrome P-450 enzymes/isoenzymes and membrane efflux transporter systems.

In a comprehensive pharmacokinetic assessment of various therapeutic agents, it was recently discovered that membrane efflux systems such as P-glycoprotein and drug-metabolizing enzymes from the cytochrome P450 isoenzyme family, as well as enzymes involved in Phase II conjugation enzyme systems, can dramatically limit clinical benefit of orally administered drugs classified by the Biopharmaceutical Classification System (BCS) in Class II, Class III and Class IV. Similarly, these proteins dramatically restrict intracellular accumulation of therapeutically effective drugs in epithelial cells following topical administration. As already discussed above, oral administration of these drugs is further limited by the fact that almost all of these drugs are associated with major gastrointestinal toxicity that patients cannot tolerate, especially when more than one agent from each class is administered as part of a combination regimen as drug cocktails. For detailed description of Class II-IV drug evaluation see Example 1.

In order to successfully treat patients life threatening clinical conditions and because of the irritating and toxic effects of the anti-cancer and/or anti-viral agents on the gastrointestinal tract, many of the agents are administered either only intravenously or, when administered orally, patients have to accept a serious gastrointestinal toxicity.

Many anti-cancer and anti-viral drugs and agents used in the therapy of cancer and HIV/AIDS are classified into one of these three categories and, consequently, one or more representative drugs belonging to one of these classes are used to illustrate the features of the current invention.

The invention thus concerns a method for augmentation of intraepithelial and/or systemic exposure to the therapeutic agents having a substrate affinity for drug-metabolizing cytochrome P-450 enzymes/isoenzymes and membrane efflux transporter systems delivered vaginally or buccally.

I. Method for Augmenting Drug Delivery to Systemic Circulation

The method of the invention provides a novel strategy to deliver the therapeutically effective drugs having a low bioavailability, specifically drugs classified in BCS Class II-IV, by either the vaginal or buccal route. The method is based on two specific and major physiological observations.

The first observation concerns findings that the vaginal and the buccal mucosa have significantly and markedly reduced expressions of the membrane efflux transporter systems and drug-metabolizing enzymes as compared to the intestinal mucosa and the liver, thereby providing conditions for a more efficient drug transport and delivery through a vaginal or buccal mucosal surface.

To illustrate experimentally the functional differences in membrane efflux activity among the intestinal, vaginal, and buccal mucosal barriers, bidirectional transport of the protease inhibitor ritonavir is quantitatively assessed and results seen in FIG. 1 may be obtained (FIG. 1). Experimental procedures are described in Example 2.

FIG. 1 is a graph that may be obtained for the intestinal barrier where the basolater to apical flux of ritonavir is 9.2-fold greater than in the opposite direction. This implies that transfer of this protease inhibitor across the intestinal mucosa is significantly restricted by functional activity of membrane efflux systems. In contrast, the $R_{efflux}$ values when calculated for the same drug across vaginal and buccal epithelium samples are significantly smaller suggesting lower expression levels of membrane efflux systems in the respective tissue barrier than in the intestine.

The second observation concerns so called second pass circulation wherein blood draining from the vaginal cavity as well as from the buccal area bypasses the liver. This second pass circulation reduces or eliminates the hepatic first pass biotransformation of the drug administered orally and mediated by concerted action of efflux transporter systems and drug-metabolizing enzymes. In fact, standard medical care for HIV/AIDS and/or cancer patients requires oral administration of various major anti-viral drugs simultaneously in so called cocktail with the intention to inhibit the action of relevant metabolizing and efflux systems by at least one of the components in this combination (cocktail) regimen. An exemplary drug of this type is ritonavir, a protease inhibitor, commercially available from Abbott Laboratories, commonly used as one component of the cocktail mixtures. The current method permits utilization of the innovative formulation strategy involving both vaginal and buccal delivery devices and/or transmucosal compositions which result in an increased portion of the active drug(s) delivered into the epithelial tissue surrounding the site of administration and/or the systemic circulation following transepithelial absorption. These new drug delivery routes allow delivery of the larger portions of the drug directly to the systemic circulation without a need for invasive intravenous injection and without the first pass metabolic deactivation of the drug in the liver. The vaginal or buccal drug delivery is thus more efficacious and provides improved therapeutic effects and better patient compliance through self-administration without the requirement of visiting a medical facility for parenteral injections.

Briefly, the method is based on physical properties of the anti-viral or anti-cancer drugs formulated as a mucosal composition for vaginal or buccal delivery. Each specific drug, based on its physical and bioavailability properties is formulated with a specific aim to increase its epithelial and/or systemic bioavailability by increasing/changing its aqueous solubility and/or permeability through the vaginal or buccal mucosa.

The mucosal composition further contains appropriate combinations of other excipients optimized for desired drug stability, bioavailability, and drug release properties.

Thus, for example, in order to achieve desirable drug release from the vaginal or buccal mucosal composition, typically, the lipophilic anti-viral or anti-cancer drug is formulated in a hydrophilic carrier and the hydrophilic anti-viral or anti-cancer drug is formulated in a lipophilic carrier. The drug is incorporated into an excipient, in this case the lipophilic or hydrophilic carrier, for which the drug has low affinity. However, there are exceptions to this principle when, for example, fast-dissolving technologies such as films and foams are applied to hydrophilic, high solubility/low permeability drugs (BCS III). The foam and film formulations comprising these drugs may be prepared using hydrophilic excipients.

To increase the solubility of the drug in the composition, and depending upon the nature of the drug, anionic, cationic or non-ionic surfactant is added. A representative anionic surfactant is, for example, sodium lauryl sulphate, representative cationic surfactants are, for example cetrimide and benzalkonium chloride and a representative non-ionic surfactants are polyoxyethylene fatty acid esters, sorbitan fatty acid esters, or glycol ethers. The solubility may be further increased by adding, polyethylene glycol, propylene glycol, cyclodextrin, etc.

The permeability can also be increased in these mucoadhesive compositions, for example, by adding penetration enhancer or sorption promoter to enhance permeation of the drug across the vaginal or buccal mucosa. Preferred sorption promoters include non-ionic surface active agents, bile salts, organic solvents, interesterified stone oil, and particularly ethoxydiglycol, commercially available, for example, as TRANSCUTOL® from Gattefosse, or interesterified stone oil, commercially available, for example, as LABRAFIL® M 1944CS from Gattefosse.

To enhance delivery efficiency of therapeutic substrates for membrane efflux transporter systems and drug-metabolizing enzymes via the vaginal and buccal route, the composition is further supplemented with non-ionizable glycol ether derivatives acting as pharmacological inhibitors of efflux transporter systems and drug-metabolizing enzymes, respectively.

Figure 2:
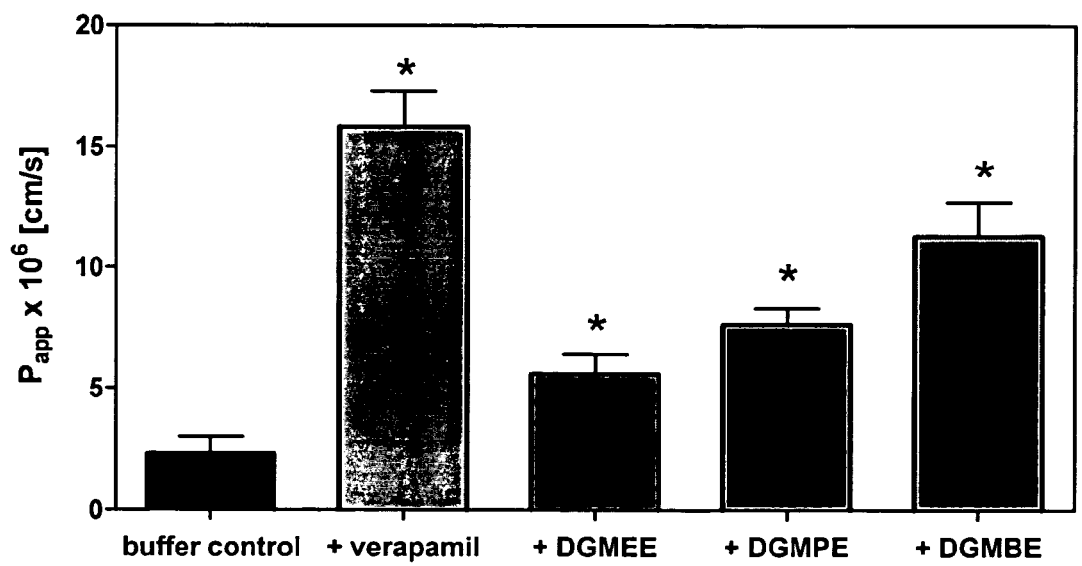
FIG. 2 is a graph that may be obtained illustrating inhibition of membrane efflux activity by glycol ethers on transepithelial transport of paclitaxel across intestinal rabbit mucosa in vitro.

An experimental demonstration of the inhibitor effect of non-ionizable glycol derivatives on functional activity of membrane efflux systems that may be obtained is included in FIG. 2. Apical to basolateral transport of the anti-cancer drug paclitaxel, which exhibits significant substrate activity for P-glycoprotein in the intestinal mucosa (Sparreboom et al., *Proc. Natl. Acad. Sci. USA*, 94, 2031-2034 (1997)), is measured across rabbit intestinal mucosa in the presence and absence of various glycol ethers and verapamil, a conventional P-glycoprotein inhibitor. Tissue perfusion studies are performed as described in Example 1 using $^{14}$C-paclitaxel.

Inclusion of verapamil (500 µM) into the transport buffer significantly increases transepithelial flux of paclitaxel by 6.4-fold. This control experiment confirms that apical to basolateral transport of this anti-cancer drug is reduced due to the activity of apically localized efflux systems such as P-gp. Similarly, inclusion of the 5% diethylene glycol mono 2-ethyl ether (DGMEE), 1% diethylene glycol monopropyl ether (DGMPE), and 1% diethylene glycol monobutyl ether (DGMBE) into the transport buffer enhances intestinal absorption of paclitaxel by 1.8-2.5, and 4.1-fold, respectively. Based on these hypothetical results, it is concluded that glycol ethers reduce functional activity of membrane efflux systems and, consequently, is suitable for use in vaginal and buccal compositions to enhance intraepithelial and/or systemic bioavailability of anti-viral and anti-cancer drugs.

To evaluate the effect of glycol ethers on cytochrome P450-mediated metabolism, enzymatic conversion of coumarin to its 7α-hydroxycoumarin oxidation product by rabbit liver microsomes in the presence and absence of 5% DGMEE, 1% DBMPE, and 1% DGMBE is determined according to a protocol described previously by Pearce and co-workers (*Arch. Biochem. Biophys.*, 298, 211-225 (1992)).

Figure 3:
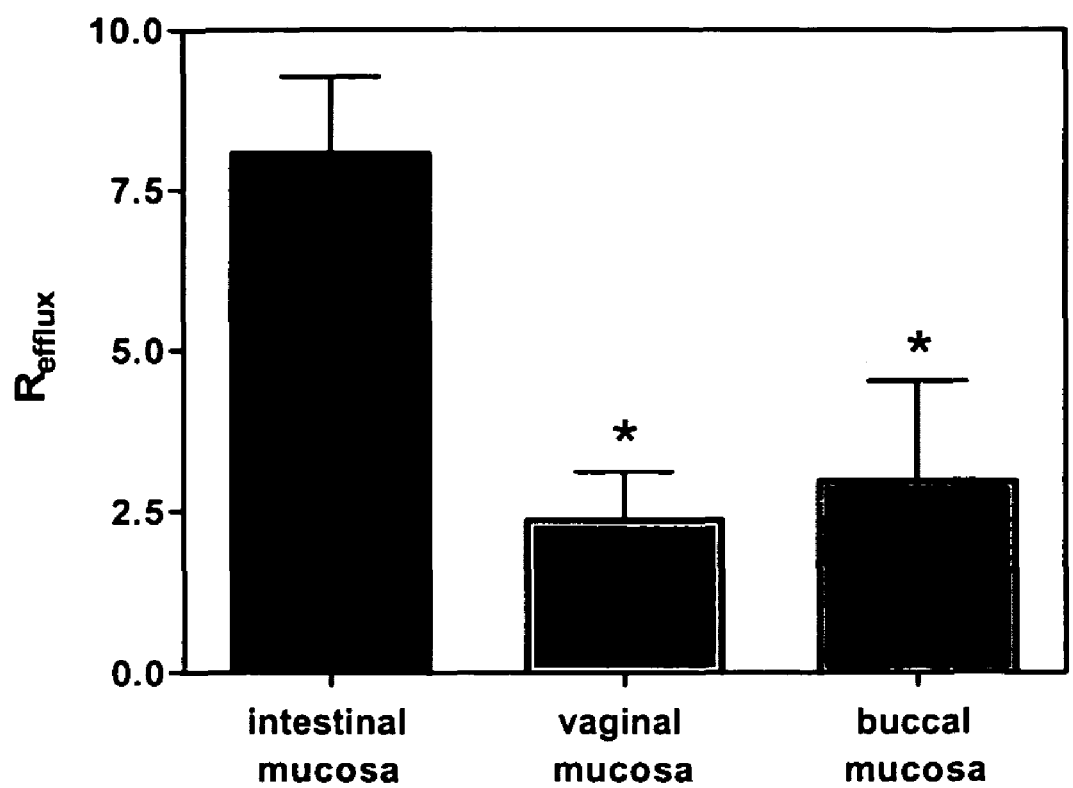
FIG. 3 is a graph that may be obtained illustrating inhibition of cytochrome P450-mediated oxidation of coumarin by glycol ethers in vitro using rabbit liver microsomes.

FIG. 3 illustrates that coumarin hydroxylation by rabbit liver microsomes is reduced after inclusion of 10 µM 8-methoxypsoralen (8-MP), a potent cytochrome P450 inhibitor. Similarly, inclusion of the various glycol ethers into the incubation mixture reduce formation of the 7α-hydroxycoumarin metabolite. Among the glycol ethers that are tested, DBMBE inhibits coumarin oxidation most potently by reducing formation of the 7α-hydroxycoumarin metabolite by about 42%. This supports the conclusion that glycol ethers have the ability to limit cytochrome P450-mediated metabolism and, consequently, enhance intraepithelial and/or systemic bioavailability of anti-viral and anti-cancer drugs that are susceptible to metabolism by members of this isozyme family when included in mucosal vaginal and buccal compositions.

Non-ionizable glycol ethers are included from about 0.01 to 50%, most preferred from 0.5 to 10%, by weight into the mucoadhesive composition as essential excipients limiting functional activity of membrane efflux systems and cytochrome P450 metabolizing enzymes, facilitating solubilization of lipophilic anti-cancer and anti-viral drugs in aqueous environment, and/or enhancing permeation across epithelial barriers into the systemic circulation. Preferred are non-ionizable glycol ethers selected from the group listed in Table 1.

The list of exemplary non-ionizable glycol ethers is seen in Table 1.

TABLE 1

Non-Ionizable Glycol Derivatives ethylene glycol monomethyl ether
diethylene glycol monomethyl ether
triethylene glycol monomethyl ether
polyethylene glycol monomethyl ether
ethylene glycol monoethyl ether
diethylene glycol monoethyl ether
triethylene glycol monoethyl ether
ethylene glycol monoisopropyl ether
ethylene glycol monobutyl ether
diethylene glycol monobutyl ether
triethylene glycol monobutyl ether
ethylene glycol monoisobutyl ether
diethylene glycol monohexyl ether
ethylene glycol mono 2-ethylhexyl ether
diethylene glycol mono 2-ethylhexyl ether
ethylene glycol monoallyl ether
ethylene glycol monophenyl ether
ethylene glycol monobenzyl ether
diethylene glycol monobenzyl ether
propylene glycol monomethyl ether
dipropylene glycol monomethyl ether
tripropylene glycol monomethyl ether
dipropylene glycol monopropyl ether
propylene glycol monobutyl ether
dipropylene glycol monobutyl ether
propylene glycol monophenyl ether
ethylene glycol dimethyl ether
diethylene glycol dimethyl ether
triethylene glycol dimethyl ether
diethylene glycol diethyl ether
diethylene glycol dibutyl ether
dipropylene glycol dimethyl ether Most preferred non-ionizable glycol derivatives are diethylene glycol monoethyl ether or ethoxydiglycol known under its trade name TRANSCUTOL®, commercially available from Gattefosse, Paramus, N.J.

To enhance intraepithelial or systemic delivery of anti-cancer and anti-viral agents following vaginal/buccal administration, functional activity of membrane efflux systems or drug-metabolizing cytochrome P450 enzymes may be inhibited by inclusion of from about 0.001 to about 10% by weight of non-toxic, purified or unpurified extracted natural products originating from plant, microorganism, or animal sources. Preferred starting materials include compounds listed in Table 2.

TABLE 2

Botanical Bioavailability Modulators

*Actaea racemosa* L. (Ranunculaceae)
*Aesculus hippocastanum* L. (Hippocastanaceae)
*Allium ampeloprasum* L. (Liliaceae)
*Allium sativum* L. (Liliaceae)
*Allium tuberosum* Rottl. (Liliaceae)
*Alpinia galangal* L. (Zingiberaceae)
*Boswellia carteri* Birdw. (Burseraceae)
*Boswellia frereana* Birdw. (Burseraceae)
*Boswellia sacra* Flueckiger (Burseraceae)
*Boswellia serrata* Roxb. (Burseraceae)
*Camelia sinensis* Kuntze (Theaceae)
*Catharanthus roseus* L. (Apocyanaceae)
*Cinnamomum burmani* Blume (Lauraceae)
*Citrus aurantium* L. (Rutaceae)
*Citrus paradisi* Macfad. (Rutaceae)
*Crataegus oxyacantha* Rehd. (Rosaceae)
*Curcuma longa* L. (Zingiberaceae)
*Echinacea angustifolia* DC. (Asteraceae)
*Echinacea pallida* Nutt. (Asteraceae)
*Echinacea purpurea* Moench. (Asteraceae)
*Eleutherococcus senticosus* Maxim. (Araliaceae)
*Foeniculum vulgare* P. Mill. (Apiaceae)
*Gingko biloba* L. (Ginkoaceae)
*Glycine max* Merr. (Fabaceae)
*Hydrastis Canadensis* L. (Ranunculaceae)
*Hypericum perforatum* L. (Clausiaceae)
*Hypoxis hemerocallidea* L. (Iridaceae)
*Matricaria recutita* L., (Asteraceae)
*Melaleuca leucadendra* L. (Myrtaceae)
*Oenothera biennis* L. (Onagraceae)
*Panax quinquefolius* L. (Araliaceae)
*Piper methysticum* G. Forst. (Piperaceae)
*Piper nigrum* L. (Piperaceae)
*Salvia miltiorrhiza* L. (Lamiaceae)
*Serenoa repens* Small (Arecaceae)
*Serenoa serrulata* Nichols (Arecaceae)
*Silybum marianum* Gaertn. (Asteraceae)
*Strychnos ligustrina* Zipp. (Loganiaceae)
*Sutherlandia frutescens* R. Br. (Fabaceae)
*Tinospora crispa* Hook. f. & Thomson (Menispermaceae)
*Uncaria tomentosa* Roxb. (Rubiaceae)
*Valeriana officinalis* L. (Valerianaceae)
*Vitis vinifera* L (Vitaceae)
*Zingiber cassumunar* Roxb. (Zingiberaceae)
*Zingiber officinale* Roscoe (Zingiberaceae)

Most preferred purified constituents isolated from the botanical bioavailability modulator sources that are incorporated into vaginal or buccal compositions between about 0.01 and about 750 mg are actein, aescin, ajmalicine, allicin, berberine, bergamottin, bergapten, bilobalide, catechin, cimiracemosides A-F, cis-linoleic acid, curcumin, desmethoxyyangonin, dihydrokavain, dihydromethysticin, fatty acid ester, genistein, guar gum, ginkolic acid I and II, 3,3',4', 5,6,7,8-heptamethoxyflavone, hydrastine, hyperforin, I3, II8-biapigenin, isobergapten, isorhemnetin, kaempferol, kavain, limonin, methysticin, naringenin, naringin, nobiletin, obacunone, oleanolic acid, pectin, piperine, quercetin, quinidine, S-allyl-L-cysteine, serpentine, silibinin, silichristin, silidianin, silybin, S-methyl-L-cysteine, sodium butyrate, tangeretin, taxifolin, ursolic acid, valerenic acid, vindoline, vintexin, 6,7-dihydroxybergamottin, and yangonin.

Generally, each mucoadhesive composition for vaginal or buccal delivery is formulated differently, depending on the properties of the anti-viral or anti-cancer drug, with an aim to achieve the maximal intraepithelial or systemic bioavailability of the drug.

The vaginal or buccal mucosal composition is delivered either as a vaginal suppository, gel, tablet, cup, cap, sponge, foam, film, strip or spray and may be either dissolvable or non-dissolvable or delivered as such or in conjunction with a vaginal or buccal device. In such an alternative, the composition is incorporated into such vaginal or buccal device or such device is covered or coated with such composition or such composition is in contact with the vaginal or buccal device. The vaginal device is a tampon, tampon-like device, pessary, ring, capsule, sponge, foam or film. The buccal device may be a sponge, foam, film, pillow, strip, capsule or a biodegradable tablet.

The dose of each agent is chosen to achieve pharmacologically effective drug concentrations. The specific transmucosal formulations have been found to permit the high bioavailability of a number of pharmacologic agents. The method of the invention consist of a combination of three independent features resulting in a cumulative effect of increased bioavailability of the drug delivered to a patient without need for an invasive procedure.

The first feature is the venous drainage path for vaginal and buccal drug delivery that bypasses the liver and the gastrointestinal tract. The venous drainage path for the vagina is into the inferior vena cava via the vaginal and uterine veins. The buccal venous draining is ultimately through the superior vena cava also bypassing the first pass effect of the gastrointestinal tract and liver.

The second feature is a lower expression of membrane efflux systems and drug-metabolizing enzymes found in the vaginal and buccal mucosa as compared to the intestinal mucosa and the liver.

The third feature, unique to the vaginal or buccal delivery and assuring greater systemic exposures of therapeutic agents with substrate affinity for membrane efflux transporter systems and drug-metabolizing enzymes than after oral administration, is inclusion of a pharmaceutically acceptable non-ionizable glycol derivative and/or botanical bioavailability modulator that inhibits functional activity of efflux transporter systems and drug-metabolizing enzymes, as well as other formulating agents and excipients, all cumulatively able to substantially increase a drug's epithelial and/or systemic bioavailability.

By advantageously combining all three above described features in the transmucosal compositions and/or devices for vaginal or buccal delivery of anti-viral or anti-cancer drugs, this invention achieves greater concentrations of these drugs in the desired target tissue or the blood circulation system. Such higher systemic concentration of the drug ultimately enhances the therapeutic benefit to the patient at a decreased risk for undesired gastrointestinal toxic side effects.

II. Therapeutically Effective Agents

Therapeutically effective agents of this invention are chemotherapeutic anti-cancer or anti-viral agents, preferably those belonging to the Classes II-IV.

The highest benefit derived from the vaginal or buccal drug delivery substituting for oral drug delivery using mucosal compositions according to the invention is observed for drugs classified in BCS Class II-IV. A list of specific anti-viral or anti-cancer drugs where the current invention provides a significant therapeutic benefit is seen in Tables 3-15.

Representative drug of the Class II are ritonavir, nelfinavir, indinavir, sequinavir and tamoxifen. Representative drug of the Class II is zalcitabine. Representative drug of Class IV is zidovudine.

Table 3 lists anti-viral agents by their brand name, generic name, abbreviation or experimental code and the source. The drugs are commercially available from the listed pharmaceutical companies.

TABLE 3

Anti-Viral Agents

| Generic Name | Brand Name/ Experimental Code | Source |
|---|---|---|
| n/a | GSK-873,140 | GlaxoSmithKline |
| n/a | PRO-542 | Progenics Pharmaceuticals |
| n/a | SCH-417690 | Schering-Plough Corporation |
| n/a | TMC278 | Tibotec Therapeutics |
| n/a | TNX-355 | Tanox, Inc. |
| α-epibromide | HE2000 ® | HollisEden Pharmaceuticals |
| Abacavir | Ziagen ® | GlaxoSmithKline |
| Aldesleukin | Proleukin ® | Chiron Corporation |
| Alovudine | MIV-310 | Boehringer Ingelheim |
| Amdoxovir | n/a | RSF Pharma, LLC |
| Amprenavir | Agenerase ® | GlaxoSmithKline |
| Atazanavir | Reyataz ® | Bristol-Myers Squibb |
| Capravirine | AG-1549 | Pfizer |
| Cidifovir | Vistide ® | Gilead Sciences, Inc. |
| Darunavir | Prezista ® | Tibotec Therapeutics |
| Delavirdine | Rescriptor ® | Pfizer |
| Dexelvucitabine | Reverset ® | Incyte Corporation |
| Didanosine | Videx ® | Briston-Myers Squibb |
| Elvucitabine | ACH-126,443 | Achillion Pharmaceuticals |
| Emtricitabine | Emtriva ® | Gilead Sciences |
| Enfuvirtide | Fuzeon ® | Trimeris/Hoffmann-La Roche |
| Erythropeoietin | Procrit ® | Ortho Biotech |
| Etravirine | TMC125 | Tibotec Therapeutics |
| Fosamprenavir | Lexiva ® | GlaxoSmithKline |
| Hydroxyurea | Droxia ® | Bristol-Myers Squibb |
| Indinavir | Crixivan ® | Merck & Co. |
| Lamivudine | Epivir ® | GlaxoSmithKline |
| Lopinavir | Kaletra ® | Abbott Laboratories |
| Maraviroc | UK-427,857 | Pfizer |
| Nelfinavir | Viracept ® | Pfizer |
| Nevirapine | Viramune ® | Boehringer Ingelheim |
| Ritonavir | Norvir ® | Abbott Laboratories |
| Saquinavir | Invirase ® | Hoffmann-La Roche |
| Somatropin | Serostim ® | Serono Laboratories |
| Stavudine | Zerit ® | Bristol-Myers Squibb |
| Tenofovir | Viread ® | Gilead Sciences |
| Tipranavir | Aptivus ® | Boehringer Ingelheim |
| Zalcitabine | Hivid ® | Hoffmann-La Roche |
| Zidovudine | Retrovir ® | GlaxoSmithKline |

Table 3 is an alphabetical list of drugs commonly used for treatment of HIV. Experimental (non-approved) drugs are italicized. FDA approved drugs for therapeutical use are in regular type.

Attachment and fusion inhibitors are a new class of anti-HIV drugs intended to protect cells from infection by HIV by preventing the virus from attaching to a new cell and breathing through the cell membrane. Therapeutically, it is expected that these drugs can prevent infection of a cell by either free virus (in the blood) or by contact with an infected cell.

Table 4 is a list of attachment and fusion inhibitors currently available either as generic or experimental drugs.

TABLE 4

Attachment and Fusion Inhibitors

| Generic Name | Experimental Code | Source |
|---|---|---|
| N/A | AK602 | Kumamoto University |
| N/A | AMD070 | AnorMed, Inc. |
| N/A | BMS-378806 | Bristol-Myers Squibb |
| Maraviroc | MVC, UK-427,857 | Pfizer |
| N/A | INCB9471 | Incyte Corp. |
| N/A | Pro 140 | Progenics Pharmaceuticals, Inc. |
| N/A | SP01A | Samaritan Pharmaceuticals, Inc. |
| N/A | TNX-355 | Tanox, Inc. |
| Vicriviroc | SCH 417690, Schering D | Schering Plough |

To combat viral more efficiently, new molecular targets are currently evaluated as future anti-viral drugs with the expectation to find another point in the HIV life cycle that can be used to inhibit viral replication and/or infections with therapeutic agents. These drugs are listed in Table 5.

TABLE 5

Other Antiretroviral Drugs

| Therapeutic Target | Experimental Code | Source |
|---|---|---|
| Integrase Inhibitor | Gilead 9137, JTK-303 | Japan Tabacco/Gilead Sciences |
| Integrase Inhibitor | MK-0518 | Merck & Co., Inc. |
| Maturation Inibitor | PA457 | Panacos Pharmaceuticals, Inc. |
| Zinc Finger Inhibitor | ADA, NSC 674447 | National Cancer Institute. |
| Antisense Drugs | HGTV43 | Enzo Theraeutics, Inc. |

Nucleoside/nucleotide reverse transcriptase inhibitors (NRTIs) are a class of anti-HIV drugs generally used in combination with other anti-HIV drugs, typically a total of three drugs in a drug cocktail. This combination is designed to block HIV replication in a patient's blood and prevent healthy T-cells in the body from becoming infected with HIV.

Table 6 is a list of anti-HIV nucleoside/nucleotide reverse transcriptase inhibitors.

TABLE 6

Anti-HIV Nucleoside/Nucleotide Reverse Trariscriptase Inhibitors

| Generic Name | Brand Name/ Experimental Code | Source |
|---|---|---|
| Abacavir | Ziagen ® | GlaxoSmithKline |
| Alovudine | MIV-310 | Boehringer Ingelheim |
| Amdoxovir | n/a | RSF Pharma, LLC |
| Dexelvucitabine | Reverset ® | Incyte Corporation |
| Didanosine | Videx ® | Briston-Myers Squibb |
| Elvucitabine | ACH-126,443 | Achillion Pharmaceuticals |
| Emtricitabine | Emtriva ® | Gilead Sciences |
| Lamivudine | Epivir ® | GlaxoSmithKline |
| Stavudine | Zerit ® | Bristol-Myers Squibb |
| Tenofovir | Viread ® | Gilead Sciences |
| Zalcitabine | Hivid ® | Hoffmann-La Roche |
| Zidovudine | Retrovir ® | GlaxoSmithKline |

TABLE 7

Anti-HIV Protease Inhibitors

| Generic Name | Brand Name/Experimental Code | Source |
|---|---|---|
| Amprenavir | Agenerase ® | GlaxoSmithKline |
| Atazanavir | Reyataz ® | Bristol-Myers Squibb |
| Darunavir | Prezista ® | Tibotec Therapeutics |
| Fosamprenavir | Lexiva ® | GlaxoSmithKline |
| Indinavir | Crixivan ® | Merck & Co. |
| Lopinavir | Kaletra ® | Abbott Laboratories |
| Nelfinavir | Viracept ® | Pfizer |
| Ritonavir | Norvir ® | Abbott Laboratories |
| Saquinavir | Invirase ® | Hoffmann-La Roche |
| Tipranavir | Aptivus ® | Boehringer Ingelheim |

Protease inhibitors listed in Table 7 are a class of anti-HIV drugs used as a one component of the combination therapy to inhibit the replication of HIV in a patient's blood. When HIV infects a cell, it copies its own RNA into the native cell's DNA. The native cell then replicate the invasive HIV DNA using a reverse transcriptase enzyme. One step in the anti- HIV treatment is to prevent such conversion of RNA into DNA by using reverse transcriptase inhibitors, such as those listed in Table 7. In the combination therapy, the protease inhibitors prevent the T-cells infected with HIV from producing new copies of the virus by blocking action of the proteases.

Table 8 summarizes information of currently FDA-approved anti-cancer agents that are clinically used in the treatment of various cancers taking advantage of various modes of action. Table 8 lists anti-cancer drugs by their brand name, generic name, abbreviation or experimental code and the source. The drugs are commercially available from the listed pharmaceutical companies.

TABLE 8

Anti-Cancer Drugs

| Generic Name | Brand Name | Source |
|---|---|---|
| Amsacrine | Amsidine ® | Parke-Davis |
| Bleomycin | Blenoxane ® | Bristol-Myers Squibb |
| Busulfan | Busulfex ® | Bedford Laboratories, Inc. |
| Capecitabine | Xeloda ® | Roche Laboratories, Inc. |
| Carboplatin | Paraplatin ® | Bristol-Myers Squibb |
| Carmustine | BiCNU ® | Bristol-Myers Squibb |
| Chlorambucil | Leukeran ® | GlaxoSmithKline |
| Cisplatin | Platinol ®-AQ | Bristol-Myers Squibb |
| Cladribine | Leustat ® | Ortho Biotech Products, L.P. |
| Crisantaspase | Erwinase ® | OPi Pharmaceuticals, |
| Cyclophosphamide | Cytoxan ® | Bristol-Myers Squibb |
| Cytarabine | Cytosar-U ® | Abraxis Pharmaceutical Products |
| Dacarbazine | DTIC-DOME ® | Bayer Pharmaceuticals |
| Dactinomycin | Cosmegen ® | Ovation Pharmaceuticals, Inc. |
| Daunorubicin | Daunorubicin ® | Bedford Laboratories, Inc. |
| Docetaxel | Taxotere ® | Bristol-Myers Squibb |
| Doxorubicin | Adriamycin ® | Bristol-Myers Squibb |
| Epirubicin | Ellence ® | Pfizer |
| Etoposide | Vepesid ® | Bristol-Myers Squibb |
| Floxuridine | FUDR ® | Mayne Pharma |
| Fludarabine | Fludara ® | Berlex Laboratories, Inc. |
| Fluorouracil | Adrucil ® | Teva Sicor Pharmaceuticals |
| Gemcitabine | Gemzar ® | Eli Lilly & Co., Inc. |
| Idarubicin | Idamycin ® | Pfizer |
| Ifosfamide | Ifex ® | Bristol-Myers Squibb |
| Irinotecan | Campto ® | Sanofi-Synthelabo |
| Leucovorin | Wellcovorin ® | GlaxoSmithKline |
| Lomustine | CeeNU ® | Bristol-Myers Squibb |
| Melphalan | Alkeran ® | GlaxoSmithKline |
| Mercaptopurine | Purinethol ® | GlaxoSmithKline |
| Mesna | Mesnex ® | Bristol-Myers Squibb |
| Methotrexate | Rheumatrex ® | STADA Pharmaceuticals, Inc. |
| Mitomycin | Mutamycin ® | Bristol-Myers Squibb |
| Mitoxantrone | Novantrone ® | Immunex Corp. |
| Oxaliplatin | Eloxatin ® | Sanofi-Synthelabo |
| Paclitaxel | Taxol ® | Bristol-Myers Squibb |
| Pemetrexed | Alimta ® | Eli Lilly & Co., Inc. |
| Pentostatin | Nipent ® | SuperGen, Inc. |
| Procarbazine | Matulane ® | Roche Laboratories, Inc. |
| Raltitrexed | Tomudex ® | AstraZeneca |
| Streptozocin | Zanosar ® | Teva Sicor Pharmaceuticals |
| Temozolomide | Temodal ® | Schering Corp. |
| Teniposide | Vumon ® | Bristol-Myers Squibb |
| Thiotepa | Thioplex ® | Bedford Laboratories, Inc. |
| Thioguanine | Tabloid ® | GlaxoSmithKline |
| Topotecan | Hycamtin ® | GlaxoSmithKline |
| Trimetrexate | Neutrexin ® | U.S. Bioscience, Inc. |
| Vinblastine | Velbe ® | Eli Lilly & Co. |
| Vincristine | Vincasar ® | Teva Sicor Pharmaceuticals |
| Vindesine | Eldisine ® | Eli Lilly & Co. |
| Vinorelbine | Navelbinev | GlaxoSmithKline |

Table 8 lists anti-cancer drugs by their generic name.

There are several groups of anti-cancer drug divided by their chemical or physiological functionality. These drugs are listed in Table 9.

TABLE 9

List of Anti-Cancer Drugs and Their Functionalities

| | |
|---|---|
| Alkylating Agents | Lomustine |
| | Carmustine |
| | Mechlorethamine |
| | Thiotepa |
| | Dacarbazine |
| | Melphalan |
| | Chlorambucil |
| | Cyclophosphamide |
| Antimetabolites | Methotrexate |
| | Trimetrexate |
| | Ara-CMP |
| | Fludarabine |
| | Hydroxyurea |
| | Fluorouracil |
| | Floxuridine |
| | Pentostatin |
| | Cyarabine |
| | Gemcitabine |
| | Thioguanine |
| | Mercaptopurine |
| DNA Cutters | Bleomycin |
| Topoisomerase I Poisons | Camptothecin |
| | Irinothecan |
| | Topotecan |
| Topoisomerase II Poisons | Daunorubicin |
| | Doxorubicin |
| | Epirubicin |
| | Idarubicin |
| | Mitoxantrone |
| DNA Binders | Dactinomycin |
| Taxol and Taxol Derivatives | Paclitaxel |
| | Docetaxel |

All the above-listed drugs as well as drugs suitable for treatment of other diseases having the same bioavailability problems may be advantageously administered by the vaginal or buccal mucosal compositions and devices using a method of the invention.

The other classes of compounds that may be administered according to the invention are, for example, bisphosphonates, such as for example, alendronate, risedronate and ibandronate; non-steroidal anti-inflammatory drugs, such as for example, diclofenac, flurbiprofen, ibuprofen and indomethacin; antiemetics, such as for example, metoclopramide and antimicrobial agents ketoconazole and rifampicin, among others.

III. Efflux Transporter and Drug-Metabolizing Enzymes and Substrates

The current invention is based on a finding that the functional activity of efflux transporter systems and drug-metabolizing enzymes of the vaginal and buccal mucosa is different than the gastrointestinal mucosa. This is an important fact for delivery of drugs classified in Class II, III and IV.

In the intestine, and similarly in other non-keratinized epithelial barrier, metabolizing enzymes such as cytochrome P4503A (CYP3A), efflux transporter proteins such as P-glycoprotein (PGP) and the multidrug resistance-associated protein (MRP2) act as an important barrier to the absorption of many clinically important drugs. Close cellular localization of efflux transporters and metabolic enzymes in the intestine indicates that these proteins function as a coordinate protective mechanism against absorption of orally administered or digested xenobiotics, chemical substances that are foreign to the biological system.

During the oral drug administration, intestinal efflux transporter systems and drug-metabolizing enzymes seem to affect substantially the rate and extent of oral absorption for drugs, particularly those with low solubility and low permeability. The low solubility and low permeability of the Class II, III and IV drugs limits the opportunity to saturate the apical efflux transporters and intestinal metabolizing enzymes and alters the expression of these transporters and enzymes. Changes in the efflux transporter expression as well as inhibition or induction of the membrane efflux and drug metabolizing proteins dramatically change the intestinal metabolism and, thus, alter the drug delivery of orally administered drugs and thus alter their systemic exposure. Cytochrome P450 3A that accounts for approximately 70% of cytochrome P450 content in the small intestine is involved in the metabolic clearance of approximately 50% of drugs currently on the market (*Drug Metab. Disp.*, 32:20-26 (2004)). P-glycoprotein, the ATP-dependent drug efflux transporter protein is responsible for active excretion of the lipophilic cationic drugs or their conjugates from liver, kidney and intestine. The multidrug resistance-associated protein 2 is involved in elimination of lipophilic anions and their conjugates. These metabolic enzymes and efflux transporters thus form important barriers to the absorption of clinically important drugs, such as anti-viral and anti-cancer agents. Characterization of the interplay between absorptive processes and intestinal metabolism revealed a large number of Class II, III and IV compounds that are primary substrates for metabolizing cytochrome P450 isozymes as well as the substrates or inhibitors of the efflux transporter P-glycoprotein. Following intestinal absorption, the systemic exposure to the orally administered drug is further limited by the interplay of a similar array of efflux systems and metabolizing enzymes in the liver. In a similar fashion, intraepithelial concentrations of topically administered drugs to the vaginal and buccal mucosa are severely limited by the concerted activity of apically expressed membrane efflux systems and intracellular cytochrome P450 isozymes.

With the exception of Class I compounds that experience a high extraction ratio and the hepatic clearance of the drug into the blood circulation, the changes in functional expression of efflux systems and metabolizing enzymes does negatively impact clinical performance of oral administration of Class II, Class III, and Class IV drugs, respectively. This is due to a direct inhibition by one or several of the drugs administered orally or through molecular regulation mechanisms induced by the drug or by the inactive excipient present in the drug formulation that affects functional activity of the efflux system or metabolizing enzyme.

Typically, every drug administered to the organism undergoes biotransformation. Such biotransformation is essential for the control and particularly termination of the drug activity and its elimination from the body. Some of the drugs thus, upon biotransformation, become inactive, if the drug itself was active, or active, if the drug was an inactive precursor.

The major site of metabolism for most drugs is the liver and the intestine and, in some cases, the kidney. Thus the drug is typically subjected to a first-pass metabolism in one of these tissues.

The first-pass metabolism, also called Phase I biotransformation, typically includes drug oxidation, reduction or hydrolysis. Phase I enzymes are found in endoplasmic reticulum.

Biosynthetic Phase II biotransformation involves a formation of a covalent linkage between a functional group of the Phase I metabolite and an endogenous molecule. Phase II enzymes are typically found in cytosol.

Phase II conjugation reactions include glucuronidation, sulfation, glutathione conjugation, acetylation, methylation, amino acid and $H_2O$ conjugation. Involved enzymes are and include UDP-glucuronsyltransferase, sulfotransferase, GSH S-transferase, acetylatransferase, methyltransferase, α-acetyltransferase and epoxide hydrolase. Drug substrates for these enzyme systems are phenols, alcohols, carboxylic acids, hydroxylamines, amines, aromatic amines, various electrophilic carbon atoms, catecholamines, aryl carboxylic acids, arene oxides, oxiranes, alkene oxides and leucotrienes $A_4$.

Phase II enzymes causing Phase II reactions are, for example, UDP-glucuronsyltrasferase resulting in glucuronide conjugation, sulfotransferase resulting in sulfation, GSH S-transferase resulting in gluthatione conjugation, acetyltransferase resulting in acetylation, methyltransferase resulting in methylation and N-acyltransferase resulting in amino acid conjugation. Drug substrates for glucuronidation are phenols, alcohols, carboxylic acids and hydroxylamines. Drug substrates for sulfation are phenols, alcohols and aromatic amines. Drug substrates for gluthatione conjugation are electrophilic carbon atoms. Drug substrates for acetylation are amines. Drug substrates for methylation are phenols, catecholamines and amines. Drug substrates for amino acid conjugation are aryl carboxylic acids.

Many of the Phase I and II enzymes are present as isoenzymes.

Biotransformation Phase I and Phase II reactions result in conversion of lipid-soluble drugs to ionically charged more soluble compounds that may be easier and more efficiently removed from the body.

Inhibition, modification or interferences with drug biotransformation results in elevated levels of the drug in the systemic circulation and in its prolonged pharmacological therapeutical effects. However, it may also result in increased drug toxicity.

Phase I and Phase II enzymes and proteins that are already found in the fetal tissue (*J. Pharmacol. Exp. Ther.*, 300(2): 361-6 (2002)) are the body's first lines of defense against cancer and HIV. These enzymes and proteins are central to the body's ability to protect itself from all manner of carcinogens and viruses that routinely enter the body through the diet, infection or the environment. However, by the same token, these enzymes and proteins also impair the treatment of these diseases by actively metabolizing the drugs having low solubility or permeability by rapidly removing these drugs from the circulation thereby limiting their therapeutic effect.

The innovative approach described herein to the anti-viral and anti-cancer drug delivery using transmucosal delivery through the vaginal or buccal mucosa, the biotransformation system of the body may be manipulated to permit greater therapeutic effect of the drugs achieved with a lesser amount of the drug, lesser toxicity and lesser occurrence of undesirable secondary symptoms associated with oral delivery of larger amounts of drugs.

IV. Transmucosal Compositions and Formulations

The method of the invention, suitable for delivery of anti-cancer and anti-viral therapy, comprises a step of providing a specifically formulated transmucosal composition comprising at least one anti-cancer or anti-viral agent, or a vaginal or buccal device incorporated with said composition, inserting said composition or device into the vagina or into the oral cavity and maintaining said composition or device in place for a period of time required for a therapeutic effect of the drug released from said mucosal composition to set in. The composition is formulated to deliver the anti-cancer or anti-viral agent to the target tissue in the surrounding epithelium or, following systemic absorption, to a different organ for treatment of cancer or HIV/AIDS. For each of the drug or treatment, the drug is formulated differently.

The method for cancer or HIV/AIDS therapy using transmucosal delivery of the drug to systemic circulation involves adding to the composition of the invention components promoting absorption and/or transport and penetration of the drug through the vaginal or buccal mucosa. Such components are added in amounts sufficient to facilitate transmucosal delivery to the general circulation.

Transmucosal treatment is based on the concept that the upper vagina and the uterus have specific blood flow characteristics, either by a portal type circulation or by venous and lymphatic channels, permitting preferential transport and delivery of the pharmacological agents from the vagina directly to the blood circulation thereby by-passing the gastrointestinal tract absorption and liver detoxification. The buccal circulation can similarly bypass liver by delivering the agent directly to vena cava superior.

The most specific demonstration of the transvaginal concept has been achieved by inventors with several types of drugs, as described in patents U.S. Pat. Nos. 6,086,909, 6,527,874, 6,905,701, 6,982,091, 6,197,327 and 6,416,779 B1, hereby incorporated by reference.

Anti-cancer or anti-viral agents, when properly formulated, are transported through the vaginal or buccal mucosa in the same manner as described in the above patents.

For topical treatment of mucosal areas close to the site of administration the formulation contains sufficient amounts of solubilizers and inhibitors of membrane efflux systems as well as drug-metabolizing enzymes to achieve therapeutically effective intraepithelial drug concentrations.

The composition is a stand alone treatment or it is incorporated into a suitable vaginal or buccal delivery device which assures the contact with the mucosa.

The composition or the medicated device according to the method is applied, that is, inserted vaginally or buccally for from about ten minutes, preferably half an hour, to several hours once, twice or several times a day or week, as needed, or according to a treatment regimen or, in alternative, it is left in place for as long as needed to achieve the drug release. The device is typically provided in dry or wet form or may be wetted prior to insertion.

The method of the invention, as described herein, provides several advantages over oral or intravenous administration of anti-cancer or anti-viral agents.

First, there is a continuous concentration of drug delivered to the vaginal or buccal mucosa and to the blood circulation bypassing the first-pass liver or intestine metabolism. This provides for a higher epithelial or systemic bioavailability of the drug and for prevention of a first-pass deactivation and elimination of the drug by the metabolic enzymes and efflux transporters present in the intestinal mucosa and the in the liver. Additionally, the device of the invention provides a continuous drug depot which allows continuous and uninterrupted delivery of drug to the vaginal mucosa over a long period of time.

Another important aspect of the invention is the reduction of side effects due to avoidance of repeated intravenous administration of the drug or inhibition of metabolic enzymes and efflux transporters.

A. Transmucosal and Mucoadhesive Compositions

A mucoadhesive composition of the invention for transmucosal delivery consists typically of five essential components. These components are: a therapeutically active anti-cancer or anti-viral agent, a lipophilic or hydrophillic carrier, a mucoadhesive agent, a non-ionizable glycol ether or botanical bioavailability modulator and sorption promoter/penetration enhancer. Additional excipients and components may be added as needed.

For topical drug delivery to the mucosal areas surrounding the vaginal or buccal sites of administration, the composition consists of at least one therapeutically active anti-cancer or anti-viral agent, a lipophilic or hydrophilic carrier, a mucoadhesive agent and the non-ionizable glycol ether or botanical bioavailability modulator. These agents are formulated either alone or in admixture with another pharmaceutical agent or a pharmaceutically acceptable excipient. All the above mentioned components of the composition must be suitable for administration to the vagina or to the buccal cavity or for incorporation into an intravaginal device for the vaginal or buccal transmucosal delivery of the drug through the mucosa into the general circulation.

The therapeutically active anti-cancer or anti-viral agent is present in an amount sufficient to assert its therapeutic effect, typically from about 0.001 to about 3000 mg, preferably from 1 to 1000 mg, most preferably from 100 to about 500 mg.

The mucoadhesive composition is typically formulated in dosage unit form, and contains a anti-cancer or anti-viral agent selected generally from drugs listed in Tables 3-15, alone, in combination, or in combination with other pharmaceutical agents or pharmaceutically acceptable components and excipients suitable for vaginal or buccal delivery to a human subject.

The composition typically contains from 0.001 to about 3000 mg, preferably from 1 to 1000 mg, of a anti-cancer and anti-viral agent with at least a 5-25% of a mucoadhesive agent promoting adhesion of the composition to the vaginal/buccal mucosa, from about 5 to about 25% of non-ionizable glycol ether and/or botanical bioavailability modulator assuring inhibition of membrane efflux system and cytochrome P450 metabolizing enzymes and from about 40 to about 95% of a lipophilic or hydrophilic carrier, depending on the drug, serving as a vehicle for the drug, and optionally, from about 0 to about 30%, preferably about 1 to 5% of a permeation enhancer or sorption promoter for transmucosal delivery of the agent through the vaginal/buccal mucosa to the systemic circulation.

Specific therapeutical anti-cancer and anti-viral drugs suitable for delivery according to this invention using the above composition are listed in Tables 3-9.

The transmucosal or mucosal composition is formulated as a cream, lotion, foam, film, ointment, suppository, liposomal suspension, microemulsion, bioadhesive microparticle, bioadhesive nanoparticle, capsule, capsule containing microparticles, solution, gel or tablet, and can be delivered as stand alone or incorporated within an vaginal/buccal device.

Alternatively, the composition can be incorporated into an vaginal/buccal device or a coating of such device, for example, a tampon or tampon-like device coating, or incorporated into a sponge, foam, film, cap, cup, pillow, strip, pessary, or other such device suitable for both the vaginal or buccal delivery. Absorbent material or matrix of such devices may be impregnated with a composition containing the drug in the form of a liquid solution, suspension, lotion, cream, microemulsions or suspensions of liposomes, bioadhesive nanoparticles, or bioadhesive microparticles. The devices of the invention are described in greater detail below in section V.

Any form of drug delivery system which will effectively deliver the anti-cancer and anti-viral agent to the mucosal area surrounding the vaginal or buccal sites of administration and transmucosally through the vaginal or buccal mucosa into the systemic circulation is intended to be included within the scope of this invention.

B. Pharmaceutical Compositions and Formulations

In order to achieve desirable drug release at a site where it is transported across the apical membrane of the epithelial cell or transmucosally through the vaginal or buccal mucosa to the systemic circulation, the anti-cancer and anti-viral is formulated in conjunction with other components which permit its epithelial adhesion of the therapeutic agent to the vaginal or buccal mucosa, facilitate transfer across the apical cell membrane containing membrane efflux systems and/or avoid intracellular drug metabolism by cytochrome P450 enzymes in order to exert its pharmacological effect within epithelium or after absorption through the vaginal or buccal mucosa at a site distant in the organism.

In addition to the therapeutic agent, a resulting composition, therefore, typically contains at least a non-toxic lipophilic or hydrophobic carrier, a mucoadhesive agent, a non-ionizable glycol ether or botanical bioavailability modulator, and optionally, a sorption promoter/permeation enhancer and/or a solubilizing agent and/or another pharmaceutically acceptable excipient suitable for vaginal or buccal delivery, such as a buffer, antioxidant, plasticizer, lubricant, filler, stabilizer, emulsifier, and any such other excipient as is known in the art to be useful for these purposes.

Any component and/or excipient used in formulations of this invention needs to be approved for human use and acceptable for use with understanding that not all excipients approved for oral use may be approved and/or suitable for vaginal use.

1. Individual Components

For vaginal/buccal transmucosal delivery, the formulation of the invention comprises the following components.

a. Anti-Cancer and Anti-Viral Agent

The anti-cancer and anti-viral agent is selected from the drugs listed in Table 3-9 and is typically present in amount sufficient to assert its desired therapeutic effect, typically from about 0.001 to about 3000 mg, preferably from about 1 to about 1000 mg, most preferably from about 100 to about 500 mg. The agent is typically either lipophilic or hydrophilic as described by its respective logP value and, depending on its affinity, it requires a different formulation protocol.

b. Lipophilic and Hydrophilic Carriers

Depending on the drug affinity, the composition of the invention additionally comprises either a lipophilic or the hydrophilic carrier that is appropriate for the pharmaceutical agent. Such carrier is typically present from about 30 to about 95%, by weight.

The carrier is selected based on chemical compatibility with the therapeutic agent and the desired release profile. In general, low affinity of the drug to the carrier corresponds to more rapid drug release.

i. Lipophilic Carriers

Preferred lipophilic carriers include hydrogenated vegetable glycerides and semisynthetic glycerides containing any medium chain triglycerides and/or a saturated mono- di- or triglyceride of fatty acids, particularly those having carbon chain of from 8 to 18 carbons, or a mixture thereof. Special grades may contain additives such as beeswax, lecithin, polysorbates, ethoxylated fatty alcohols, and partially ethoxylated fatty glycerides. Examples of the lipophilic carrier are saturated glycerides known and available under the trade name SUPPOCIRE® AS2 or CS2, and related compounds commercially available, for example, from Gattefosse, Paramus, N.J.

ii. Hydrophilic Carriers

Preferred hydrophilic carriers include polyethylene glycols of molecular weight between about 200 and 8000, low-viscosity cellulose derivatives such as methylcellulose and hydroxypropyl methylcellulose having molecular weights between 10,000 and 100,000, alginic acid and its salts and esters such as sodium alginate or propylene glycol alginate, partially hydrolyzed polyvinyl alcohol, and polyethylene oxides of molecular weight between about 100,000 and 9,000,000 commercially available from, for example, Dow Chemical Company, Midland, Mich. In addition, derivatives and copolymers of such chemically related homomers, including PEG 6000/PEG 1500, or PEG 6000/PEG 1500/PEG 400, or PEG 6000/PEG 400, or PEG 8000/PEG 1500 (commercially available from, for example, Sigma/Aldrich, St. Louis, Mo.) or chemically unrelated homomers such as polyethylene glycol and acrylic acid, vinyl acetate, and methyl acrylate may be used.

c. Mucoadhesive Agent

For transmucosal delivery, the composition comprises, as an essential component, a mucoadhesive agent. The mucoadhesive agent permits a close and extended contact of the composition, or the drug released from said composition, with mucosal surface by promoting adherence of said composition or drug to the mucosa. The mucoadhesive agent is preferably a polymeric compound, such as preferably, a cellulose derivative but it may be also a natural gum, alginate, pectin, or such similar polymer. The most preferred cellulose derivative is hydroxypropyl methylcellulose available under the trade name METHOCEL®, commercially available from Dow Chemical Co.

The mucoadhesive agent is present in from about 5 to about 25%, by weight, preferably in from about 10 to about 15% and most preferably about 10%.

d. Non-Ionizable Glycol Ethers

The mucoadhesive composition additionally includes a non-ionizable glycol ether present in from about 0.01 to about 50%, most preferred from about 0.5 to about 10%, by weight. The glycol ether is an essential excipients limiting functional activity of membrane efflux systems and cytochrome P450 metabolizing enzymes. Furthermore, the surface-active properties of non-ionizable glycol ethers facilitate solubilization of lipophilic anti-cancer and anti-viral drugs in aqueous environment and enhances permeation across epithelial barriers into the systemic circulation. Preferred are non-ionizable glycol ethers selected from the group consisting of ethylene glycol monomethyl ether, diethylene glycol monomethyl ether, triethylene glycol monomethyl ether, polyethylene glycol monomethyl ether, ethylene glycol monoethyl ether, diethylene glycol monoethyl ether, triethylene glycol monoethyl ether, ethylene glycol monoisopropyl ether, ethylene glycol monobutyl ether, diethylene glycol monobutyl ether, triethylene glycol monobutyl ether, ethylene glycol monoisobutyl ether, diethylene glycol monohexyl ether, ethylene glycol mono 2-ethylhexyl ether, diethylene glycol mono 2-ethylhexyl ether, ethylene glycol monoallyl ether, ethylene glycol monophenyl ether, ethylene glycol monobenzyl ether, diethylene glycol monobenzyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, propylene glycol monophenyl ether, ethylene glycol dimethyl ether, diethylene glycol dimethyl ether, triethylene glycol dimethyl ether, diethylene glycol diethyl ether, diethylene glycol dibutyl ether and dipropylene glycol dimethyl ether, most preferably, diethylene glycol monoethyl ether or ethoxydiglycol, known under its trade name TRANSCUTOL® and commercially available from Gattefosse, Paramus, N.J.

e. Botanical Bioavailability Modulators

To enhance intraepithelial or systemic delivery of anti-cancer and anti-viral agents following vaginal/buccal administration, functional activity of membrane efflux systems or drug-metabolizing cytochrome P450 enzymes may be inhibited by inclusion of 0.001-10% by weight of non-toxic, purified or unpurified extracted natural products originating from plant, microorganism, or animal sources. Preferred starting materials include *Actaea racemosa* L. (Ranunculaceae), *Aesculus hippocastanum* L. (Hippocastanaceae), *Allium ampeloprasum* L. (Liliaceae), *Allium sativum* L. (Liliaceae), *Allium tuberosum* Rottl. (Liliaceae), *Alpinia galangal* L. (Zingiberaceae), *Boswellia carteri* Birdw. (Burseraceae), *Boswellia frereana* Birdw. (Burseraceae), *Boswellia sacra* Flueckiger (Burseraceae), *Boswellia serrata* Roxb. (Burseraceae), *Camelia sinensis* Kuntze (Theaceae), *Catharanthus roseus* L. (Apocyanaceae), *Cinnamomum burmani* Blume (Lauraceae), *Citrus aurantium* L. (Rutaceae), *Citrus paradisi* Macfad. (Rutaceae), *Crataegus oxyacantha* Rehd. (Rosaceae), *Curcuma longa* L. (Zingiberaceae), *Echinacea angustifolia* DC. (Asteraceae), *Echinacea pallida* Nutt. (Asteraceae), *Echinacea purpurea* Moench. (Asteraceae), *Eleutherococcus senticosus* Maxim. (Araliaceae), *Foeniculum vulgare* P. Mill. (Apiaceae), *Gingko biloba* L. (Ginkoaceae), *Glycine max* Merr. (Fabaceae), *Hydrastis Canadensis* L. (Ranunculaceae), *Hypericum perforatum* L. (Clausiaceae), *Hypoxis hemerocallidea* L. (Iridaceae), *Matricaria recutita* L., (Asteraceae), *Melaleuca leucadendra* L. (Myrtaceae), *Oenothera biennis* L. (Onagraceae), *Panax quinquefolius* L. (Araliaceae), *Piper methysticum* G. Forst. (Piperaceae), *Piper nigrum* L. (Piperaceae), *Salvia miltiorrhiza* L. (Lamiaceae), *Serenoa repens* Small (Arecaceae), *Serenoa serrulata* Nichols (Arecaceae), *Silybum marianum* Gaertn. (Asteraceae), *Strychnos ligustrina* Zipp. (Loganiaceae), *Sutherlandia frutescens* R. Br. (Fabaceae), *Tinospora crispa* Hook. f. & Thomson (Menispermaceae), *Uncaria tomentosa* Roxb. (Rubiaceae), *Valeriana officinalis* L. (Valerianaceae), *Vitis vinifera* L (Vitaceae), and *Zingiber cassumunar* Roxb. (Zingiberaceae), *Zingiber officinale* Roscoe (Zingiberaceae).

Most preferred purified constituents isolated from those above listed sources that are incorporated into vaginal or buccal compositions in between about 0.01 and about 750 mg are actein, aescin, ajmalicine, allicin, berberine, bergamottin, bergapten, bilobalide, catechin, cimiracemosides A-F, cis-linoleic acid, curcumin, desmethoxyyangonin, dihydrokavain, dihydromethysticin, fatty acid ester, genistein, guar gum, ginkolic acid I and II, 3,3',4',5,6,7,8-heptamethoxyflavone, hydrastine, hyperforin, 13, I18-biapigenin, isobergapten, isorhemnetin, kaempferol, kavain, limonin, methysticin, naringenin, naringin, nobiletin, obacunone, oleanolic acid, pectin, piperine, quercetin, quinidine, S-allyl-L-cysteine, serpentine, silibinin, silichristin, silidianin, silybin, S-methyl-L-cysteine, sodium butyrate, tangeretin, taxifolin, ursolic acid, valerenic acid, vindoline, vintexin, 6,7-dihydroxybergamottin, and yangonin.

f. Sorption Promoters/Penetration Enhancers

To facilitate permeation of anti-cancer and anti-viral agents across the non-keratinized epithelial barrier into the systemic blood circulation transmucosal compositions additionally include at least one sorption promoter/penetration enhancer, usually present in from about 0.001 to about 30% by weight. Sorption promoters include non-ionizable glycol ethers as included in Table 1, as well as glycol ester derivatives such as polyethylene glycol caprylic/capric glycerides known as LABRASOL® from Gattefosse, and glycol derivatives with glycerol esters, such as oleic acid esters of propylene glycol and glycerol known as ARLACEL® 186 from Imperial Chemical Industries. Particularly preferred are non-ionizable glycol ether derivatives, such as, or interesterified stone oil, for example LABRAFIL M 1944CS, commercially available from Gattefosse. The interesterified stone oil is a vegetable oil ethoxylated by replacing part of glycerol of the glycerides contained in vegetable oil by polyoxyethylene-glycols.

Especially preferred are non-ionizable glycol ethers selected from the group consisting of ethylene glycol monomethyl ether, diethylene glycol monomethyl ether, triethylene glycol monomethyl ether, polyethylene glycol monomethyl ether, ethylene glycol monoethyl ether, diethylene glycol monoethyl ether, triethylene glycol monoethyl ether, ethylene glycol monoisopropyl ether, ethylene glycol monobutyl ether, diethylene glycol monobutyl ether, triethylene glycol monobutyl ether, ethylene glycol monoisobutyl ether, diethylene glycol monohexyl ether, ethylene glycol mono 2-ethylhexyl ether, diethylene glycol mono 2-ethylhexyl ether, ethylene glycol monoallyl ether, ethylene glycol monophenyl ether, ethylene glycol monobenzyl ether, diethylene glycol monobenzyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, propylene glycol monophenyl ether, ethylene glycol dimethyl ether, diethylene glycol dimethyl ether, triethylene glycol dimethyl ether, diethylene glycol diethyl ether, diethylene glycol dibutyl ether and dipropylene glycol dimethyl ether.

Penetration enhancers are thus compounds which assist in improving penetration properties of the drug or their mixtures by changing the surface properties of the drugs or their mixtures, or drug containing solutions or suspensions. These compounds thus, in a way act as solubilizers.

g. Solubilizing Agents

The composition optionally includes also a solubilizing agent, such as complex-forming solubilizer citric acid, ethylenediamine-tetraacetate, sodium meta-phosphate, succinic acid, urea, cyclodextrin, polyvinylpyrrolidone, diethylammonium-ortho-benzoate or micelle-forming solubilizers such as Tweens and Spans, for example Tween 80. Other solubilizers useful for the compositions of this invention are polyoxyethylene sorbitan fatty acid ester, polyoxyethylene n-alkyl ethers, n-alkyl amine n-oxides, poloxamers, organic solvents, phospholipids and cyclodextrines.

h. Additional Excipients

The composition of the invention may additionally contain other excipients, such as, buffers, antioxidants, plasticizers, lubricants, fillers, stabilizers, emulsifiers, and others as appropriate. Examples of these excipients are water soluble inorganic and organic salts of acetic, ascorbic, carbonic, citric, lactic, and sorbic acid, acetyltriethyl citrate, butylated hydroxyanisole, butylated hydroxytoluene, carbomer 934P or 940, erythorbic acid, glycerin, glycerides, hydrogenated palm oil, isostearylstearate, isopropyl myristate, mannitol, mineral oil, polycarbophil, propylene glycol, propyl gallate, purified water, sodium hydroxide, sorbitol, α-tocopherol, α-tocopheryl polyethylene glycol 1000 succinate, thymol, and triacetin.

2. Preferred Formulations

Any and all formulations which contains components of the invention in ranges given above are intended to be within the scope of this invention. Few compositions presented here as preferred formulation are only exemplary and are not intended to limit the scope of the invention in any way.

Preferred formulations for the immediate release of hydrophilic anti-cancer and anti-viral drugs comprise between about 0.01-10%, by weight, of the drug, about 30-90%, by weight of hydrophilic carrier, between about 1-25%, by weight, of mucoadhesive agent, between 0.01 and 25% of a non-ionizable glycol ether or botanical bioavailability modulator, and optionally between about 25-65% of buffering agents, and 0.001-5%, by weight, of a solubilizing agent and/or permeation enhancer.

Preferred formulations for time-delayed release of hydrophilic anti-cancer and anti-viral drugs comprise between about 0.01-10%, by weight, of the drug, about 60-90%, by weight, lipophilic carrier, between about 5-25%, by weight, mucoadhesive agent, between about 1-25%, by weight, of a non-ionizable glycol ether or botanical bioavailability modulator and optionally an antioxidant, buffering agents, a penetration enhancer, or solubilizing agent, usually present in 0.005-30%, by weight.

In another preferred embodiment of the invention, 0.01-10% of the drug is formulated with other components such as between 60 to 90%, by weight, lipophilic carrier, between about 5 and about 20% mucoadhesive agent, between about 10 and about 20% of a non-ionizable glycol ether, between about 0 and about 30% solubilizing agent, between about 0.01 to about 5% permeation enhancer and between about 0.01 and about 4% antioxidant.

Preferred formulations for hydrophilic anti-cancer and anti-viral drugs comprise between about 0.01-10%, by weight, of the drug, about 60-90%, by weight, lipophilic carrier, between about 5-25%, by weight, mucoadhesive agent, between about 1-25%, by weight, sorption promoter and optionally a penetration enhancer or solubilizing agent, usually present in 1-30%, by weight.

Preferred formulations for the lipophilic anti-cancer and anti-viral drugs comprise between about 0.01-10%, by weight, of the drug, about 30-90%, by weight of hydrophilic carrier, between about 1-25%, by weight, of mucoadhesive agent, between 1 and 25% of sorption promoter and optionally between about 1-30%, by weight, solubilizing agent and/or permeation enhancer.

In another preferred embodiment of the invention, 0.01-10% of the drug is formulated with other components such as between about 30 and about 60%, by weight, lipophilic carrier, between about 5 to 20% mucoadhesive agent, between about 1 and about 15% of non-ionizable glycol ether and, optionally, between 0 and about 10% of solubilizing agent and between about 35 and about 65% of buffering agents.

In another preferred embodiment of the invention, 0.01-10% drug is formulated in admixture with about 60 to 90%, by weight, of hydrophilic carrier, between about 5 and about 20% of mucoadhesive agent, between about 10 and 15% of sorption promoter and optionally between 0-30% of solubilizing agent and/or between about 1 and 30% of permeation enhancer.

In another preferred embodiment of the invention, the drug is formulated as a vaginal suppository or buccal pellet which includes 0.01-10% of a drug, 75% of a lipophilic carrier SUPPOCIRE® AS2, 2% hydroxypropyl methylcellulose, and 15% of ethoxydiglycol (TRANSCUTOL®). The suppository may be a stand-alone device or be incorporated into a tampon or tampon-like device.

In another preferred embodiment of the invention, the drug is formulated as a vaginal or buccal mucoadhesive film which includes about 0.01-10% of a drug, about 45-55% of a hydrophilic carrier such as PEG 6000/polyethylene oxide 200,000, about 25% hydroxypropyl methylcellulose, and 15% of ethoxydiglycol (TRANSCUTOL®). The film may be a stand-alone device or be incorporated into or covering another device.

In yet another preferred embodiment of the invention, the BCS III drug having a low permeability and high solubility formulated in a fast dissolving foam or film is prepared using mucoadhesive, hydrophilic excipients with incorporated non-ionizable glycol ether and/or botanical bioavailability modulator, respectively.

3. Process for Formulating Hydrophilic or Lipophilic Drugs

The lipophilic or hydrophilic anti-cancer and anti-viral agents are formulated using the following process.

In a general method for preparing a drug formulation with a lipophilic carrier, the hard fat suppository base is melted at 45-50° C. in a heated vessel. The mucoadhesive agent is added to the carrier under vigorous stirring. The preferred hydrophilic drug is dissolved in the non-ionizable glycol ether, combined with the botanical bioavailability modulator, and the antioxidant.

This mixture is added to the carrier/mucoadhesive agent suspension. The final formulation is poured into molds of the desired size and shape or incorporated into a device of the invention. The molds which are stored in a refrigerator at 4-6° C. In a general method for preparing a formulation including a drug in a hydrophilic carrier, the water soluble polymer is dissolved with the mucoadhesive agent and the buffer components in water. This solution is combined with a drug solution containing the non-ionizable glycol ether, antioxidant and, optionally, a solubilizing agent, and/or penetration enhancer. This film precursor solution is dried using a gel dryer. The remaining film is carefully peeled off the glass plate and cut in defined dose units.

4. Sustained Release

In one embodiment, the composition can be formulated as a sustained and controlled release drug system.

The drug which is formulated for controlled and sustained release is formulated either for continuous release or for pulsed delivery.

Continuous release or delivery means continuous and uninterrupted release of the drug from the formulation or device wherein the drug is formulated either in the matrix, microparticle, bioadhesive particle, liposomal suspension or any another system typically used for such release.

Pulsed release or delivery is a delivery of the drug in intermittent intervals. Such pulsed delivery may be provided, for example, by formulating the drug in the matrix, microparticle, bioadhesive particle, liposomal suspension or any another system, as described for continuous delivery, in individual layers interspaced with inactive layer of inactive, for example, dissolvable coatings or by using different formulating agents. Methods and formulating agents for sustained delivery are known in the art.

The controlled release, a drug delivery system must be capable of controlled release of a drug into the vaginal/buccal mucosa over several minutes, hours or longer. This is achieved by the addition of time release additives such as hydrogel-forming polymers, non-erodible matrices, etc., known in the art.

Additionally, to accommodate drug-specific ionization properties at the site of administration, the drug delivery systems additionally may contain buffers to stabilize pH preferentially to enhance absorption. Furthermore, antioxidants may be incorporated to increase chemical stability of the drug in the composition.

The sustained release composition of the invention is typically in a form of a cream, lotion, foam, film, suppository, tablet, microparticle, nanoparticle, capsule containing microparticles, liposomal suspension fluid, bioadhesive systems and microemulsions.

5. Bioadhesive Systems and Microemulsions

Bioadhesive systems and microemulsions are formulations particularly suitable for topical and transmucosal delivery of anti-cancer and anti-viral drugs following administration to the vaginal and/or buccal cavity.

The microemulsion may contain pharmaceutically acceptable surfactants, for example, LABRASOL®, PLUROL® isostearate (Gattefossé), co-solvents such as isopropanol or ethanol, and water. Microemulsions containing one or several of the above components have been shown to improve bioavailability of anti-cancer and anti-viral drugs.

Bioadhesive microparticles or bioadhesive nanoparticles constitute still another intravaginal drug delivery system suitable for use in the present invention.

The bioadhesive systems use derivatives of cellulose such as hydroxypropyl cellulose and polyacrylic acid. They release the pharmacological agent for up to five days once they are placed in the appropriate formulation. The microparticles or nanoparticles cling to the vaginal/buccal mucosa and release the drug slowly over a period of several hours to several days. Many of these systems were designed for nasal use, as described in U.S. Pat. Nos. 4,756,907, and 6,200,590 incorporated herein by reference, but can be easily modified for use in the vagina/buccal cavity. The bioadhesive system may comprise microparticles or nanoparticles filled with the anti-cancer and anti-viral drugs and may contain a surfactant for enhancing solubility and/or uptake of the drug. The microparticles have a diameter of 1-100 µm, whereas nanoparticles have a diameter of 10-1000 nm. Microparticles and nanoparticles can be prepared from natural polymers, such as starch, gelatin, albumin, collagen, and/or dextrans, synthetic polymers, such as poly(lactide-co-glycolide), sodium acrylate, poly lactic acid, polyethylene glycol, or mixtures thereof, including inulin multi-methacrylate, cystine bisacrylamide, according to methods known in the art.

Bioadhesive tablets are another drug delivery system suitable for transmucosal delivery. These bioadhesive systems use hydroxypropyl cellulose and polyacrylic acid. They release drugs for up to five days once they are placed in the appropriate formulation. The tablet of the invention is most preferred adapted in shape to maximize surface contact between the vaginal/buccal mucosa and the tablet. It may have such a shape as is suitable for incorporation into the device.

The drug can also be incorporated into creams, lotions, foams, films, paste, ointments, microemulsions, liposomal suspensions, and gels which can be administered to the vaginal/buccal cavity using an applicator. Processes for preparing pharmaceuticals in these vehicles can be found throughout the literature.

Suitable nontoxic pharmaceutically acceptable excipients for use in the compositions of the present invention will be apparent to those skilled in the art of pharmaceutical formulations and examples are described in *REMINGTON: The Science and Practice of Pharmacy*, 20$^{th}$ Edition, A. R. Gennaro, ed., (2000). The choice of suitable carriers will depend on the exact nature of the particular dosage form desired, e.g., whether the anti-cancer and anti-viral agent is to be formulated into a cream, lotion, foam, film, ointment, paste, solution, microemulsions, liposomal suspension, microparticles, nanoparticles, gel or tablet, as well as on the physicochemical properties of the active ingredient(s) and the desired release kinetics.

Although the compositions described above typically contain one pharmaceutically active ingredient from the group of anti-cancer and anti-viral agents for treatment of cancer and HIV/AIDS, such compositions may additionally contain other pharmaceutical agents or a combination thereof, such as, for example, analgesics, anti-virals, antipruretics, corticosteroids and other agents which may enhance the therapeutic effect of the primary drug.

All bioadhesive systems described above may be administered directly or via the vaginal/buccal device.

II. Devices for Vaginal/Buccal Delivery of Therapeutical Agents

The device of the invention, such as a vaginal tampon, vaginal tampon-like device, vaginal foam, vaginal film, vaginal sponge, vaginal pessary, vaginal suppository, vaginal tablet, vaginal pellet or vaginal ring, or buccal foam, buccal film, buccal sponge, buccal pessary, buccal suppository, buccal tablet or buccal pellet, provides an improvement against previously described devices. In particular, the device of the invention, which is preferably a degradable or non-degradable device, coated completely or, preferably, only partly at its proximal or distal end or in the middle with a layer or layers of a coating, covering or is combined with such covering. The coating may be in the form of a film, foam, sponge, strip, cup, cap or particle or it may be a covering in the form of a foam, film, strip, cap, cup or pellet, tablet or suppository attached, as described or illustrated in the figures.

The material may be applied to the device as one layer or several layers interspaced with a layer or layers of different material, it may form a cap or cup covering a proximal or distal portion of the tampon, pellet or tablet, or it may be a strip, string or rim of the coating encircling the tampon. Since the vaginal tampon or vaginal foam is made of porous material, usually a cotton or polymer, the coating material covering at least a proximal portion, typically the proximal end of the tampon, separates the porous material from the material coated with the coating layer and sequesters the portion of such porous material from the portion comprising the anti-cancer or anti-viral therapeutical agent within the coating. The coating, whether the layer, layers, strip, strips, cap or cup, foam or film is incorporated with a mucoadhesive composition comprising a therapeutic agent or such composition is attached to such coating by various means.

The coating of the entire device prevents the absorption of the mucoadhesive composition into the porous portion of the device. The partial coating of the device permits sequestration of the drug to a smaller area and prevents the absorption of the mucoadhesive composition into the porous portion of the device. Thus, the loss of the drug due to reabsorption into the porous portion of the device is either eliminated or substantially decreased. Additionally, since the mucoadhesive composition comprising the therapeutical is sequestered within the coating applied to the proximal end of the device, it is preferentially released from the device into the vicinity of uterus where the mucosal epithelia is more apt to absorb the agent.

The drug is therefore delivered more quantitatively to the mucosa to which it adheres due to the presence of the mucoadhesive agent from where it is distributed into the surrounding epithelium or is transported through the mucosa to the general systemic circulation due to the presence of the sorption promoter and/or penetration enhancer. The lipophilic or hydrophilic carrier additionally modifies the drug interaction with the mucosal surface and enhances the drug surface exposure.

A. Coated Vaginal Devices

The vaginal device of the invention is a vaginal tampon, dissolving or non-dissolving, degradable or non-degradable vaginal tampon or tampon-like shaped device, such as a vaginal foam, vaginal film, vaginal sponge, vaginal ring, vaginal suppository, vaginal tablet, vaginal pellet or vaginal pessary, all coated or at least partially coated with a layer of coating separating the body of the device from the mucosal composition incorporated into or attached to said coating. The most preferred embodiment is a vaginal tampon or the tampon-like shaped device or foam.

A variation of the vaginal tampon is prepared in the same manner for buccal use accommodating specific anatomical and physiological requirements of the oral cavity.

1. Vaginal Tampon

One preferred embodiment for vaginal drug delivery is the vaginal tampon. The vaginal tampon is typically a commercially available vaginal tampon that is coated, according to the invention, either completely or partially, typically to about one third or one half, that is a portion coming in contact with the vaginal wall. The proximal or distal end, or a middle portion of the tampon is coated with a coating forming a layer, layers, cap, cup, film, foam, particles or strip around the upper proximal top portion of the tampon or attached to the tampon as a covering in the form of a cap, cup, strip, foam, film, tablet, suppository, soft gel capsule or pellet prepared separately. However, the whole tampon may also be coated with the coating, if desirable and the composition is then attached to the whole, to the proximate or distal part, or to the tip of the tampon.

2. Vaginal Foam

Another preferred embodiment is a tampon-like shaped vaginal foam that may be fully or partially dissolving or non-dissolving or degradable in the vagina or it may be non-degradable. However, the foam may also be shaped differently than a tampon-like structure.

The foam used as a vaginal device is preformed into a specific shape of a solid structure or a semi-solid or liquid preparation. The latter two may be used as a receptacle for the mucoadhesive composition which is applied in a form of a foam, film or particle layer, strip, cup or cap coating into which the composition may be conveniently incorporated.

The vaginal foams, as well as films, whether degradable or non-degradable and whether used as a vaginal device or a coating therefore, are prepared by processes known in the art that introduce porosity in a polymer matrix, namely by lyophilization, aeration, freeze drying, hydrocarbon templating, salt or particulate leaching, gel or solvent casting, gas expansion, sintering, polymerization of high internal phase emulsions, and free form fabrication techniques such as three-dimensional polymer printing.

The most preferred process to fabricate foams is lyophilization, which is described in detail in the copending application Ser. No. 10/600,849 filed Jun. 30, 2003, incorporated herein by reference. Lyophilized foams are open cell, high-surface-area, biodegradable or non-degradable constructs that can be manufactured from a variety of polymers, preferably from hydrophilic polymers. The foam materials are characterized by controlled chemical and physical properties that can be tailored according to their intended application. Tuneable properties include hydrophilicity, rate of absorption, degradation profile and dissolution rate, a measure of which is the time needed to complete dissolution of the foam.

Typically, the lyophilized foam is prepared by dissolving an appropriate polymer, preferably a hydrophilic polymer, or a mixture thereof, serving as a substrate material, as listed below, in an amount needed to prepare solution from 1 to 10% (w/w) in an aqueous or non-aqueous solvent, such as methanol, ethanol, glycerine, methylene, chloride, propylene glycol, propylene carbonate, glycofurol, cetyl alcohol, difluoroethane and isopropylalcohol, preferably a purified water.

Alternatively, polymeric solutions with the drug and additives may be prepared in acetic acid, cyclohexane, acetonitrile, tert-butanol, ethanol, and isopropanol or in mixtures of aqueous and non-aqueous solvents.

Substrate materials for preparation of foam compositions of the invention are hydrophobic or, preferably, hydrophilic polymers. These polymers may be used singly or in combination with each other. They may be used in variable concentrations and ratios to each other when in admixture of two or several polymers.

Non-exclusive list of substrate polymers comprises cellulose and cellulose derivatives, microcrystalline cellulose, polyacrylic acid, polyethylene glycol, polypropylene glycol, divinyl glycol, polyethylene oxide, polypropylene oxide. Other possible polymers include the cellulose derivatives such as carboxymethyl cellulose, hydroxyethyl cellulose, polylactide, polyglycolide, polymethacrylic acid, poly-γ-benzyl-L-glutamate, polypropylene fumarate, poly-ϵ-caprolactone, poly-butylene terephthalate, polyvinyl alcohol, polyvinyl ether, poly-1-vinyl-2-pyrrolidinone, 2,5-dimethyl-1,5-hexadiene, divinyl benzene, polystyrene-divinyl benzene, polyanhydrides such as poly-bis-p-carboxy-phenoxypropane-co-sebacic acid, polyhydroxyalkanoates such as poly-β-hydroxybutyrate or poly-β-butyrolactone, and alkyl-substituted silica gel such as tetraethylorthosilicate and dimethyldiethoxysilane.

Examples of hydrophilic polymers suitable for a foam manufacture include hydroxypropyl methylcellulose (HPMC), sodium carboxymethylcellulose, polyethylene glycol (PEG), alginic acid, alginic acid sodium salt, pectin, gelatin, collagen, polyvinyl pyrrolidone, poloxamer, acrylic-acid based polymers, such as carbopol, noveon, polyurethanes, polyvinyl alcohol, chitosan, hydroxypropyl cellulose, polyethylene oxide, fibronectin, hyaluronic acid, polysaccharide gums such as karaya gum, polyacrylamide, polycarbophil, dextran, xanthan gum, polyacrylamide, polyacrylamide, crosslinked polymethyl vinyl ether-co-maleic anhydride, commercially available as Gentrez™, gelatin, corn starch and mixtures thereof.

Examples of hydrophobic polymers suitable for formation of the foam are, among others, polypropylene oxide, polyamides, polystyrene, and polymethacrylic acid.

Tampon-like vaginal foams that undergo dissolving or degradation in the vagina into smaller units or polymers by various mechanisms are classified as degradable or dissolving foam. This type of the foam is preferred as long as their degradation or dissolving is controlled and coincides with or exceeds the time needed for a complete release of the drug from the coating attached to the degradable or dissolving vaginal foam.

Non-degradable or non-dissolving vaginal foams are the foams resisting a degradation of the three-dimensional structure. Representative but not limiting examples of non-biodegradable or non-dissolving polymers that may be used exclusively, or in alternative that may be also coated with biodegradable or dissolving polymeric foams, include polyamides, polyethylene, polypropylene, polystyrene, polyvinyl chloride, polymethacrylic acid, and derivatives thereof alone or as co-polymeric mixtures thereof.

Both dissolving or non-dissolving, degradable or non-degradable foams may be prepared in a range of sizes and a variety of shapes suitable for use as a vaginal device or the coating thereof, including foam pillows, tubes, cylinders, spheres, tablets or rings (devices) or films, sheets or beads or any other desirable shape (coating) using an appropriate processes known in the art that introduce porosity in a polymer matrix.

The foam as a vaginal device is preformed into a device such as a tampon, tampon-like cylinder, strip, pad, pillow, tube, sphere, tablet or ring or any other shape as might be desirable or it may be applied as a film, sheet or beads, as a coating to a surface of a more complex vaginal device made of a different material, such as, for example, a conventional vaginal tampon, tampon-like device, pessary, ring, strip, pad, pillow, sheet, tube, sphere or tablet covered by said coating foam. In this configuration the foam is applied as a receptacle for the mucoadhesive composition as described in greater detail in the coating section below.

A variation of the vaginal tampon-like device is prepared in the same manner for buccal use using materials and method for their preparation.

3. Vaginal Film

Another embodiment of the invention concerns a polymer formulated into a film for topical or transepithelial vaginal or buccal delivery of therapeutic agents. The polymer films of the invention are high-surface-area sheets that are prepared from a variety of polymer solutions which are processed into a film.

Similarly to the foams, films of the invention are characterized by their controlled chemical and physical properties that can be tailored according to their intended application. Tuneable properties include hydrophilicity, rate of fluid absorption and degradation profile including a dissolution rate. The films of the invention thus release the active ingredient by dissolution or erosion or a combination of these mechanisms which may depend on interaction of the film composition with components at the site of administration, including but not limiting to fluid and ions. This will attain desired bioadhesive properties of the film and control the release rate of the agent as required by the therapeutic regimen for hours or days.

Typically, the film is prepared by dissolving an appropriate polymer, preferably a hydrophilic polymer, or a mixture thereof serving as a substrate material, as listed below, in an amount needed to prepare a solution of from about 1 to about 10% (w/w), in an aqueous or non-aqueous solvent, such as methanol, ethanol, glycerine, methylene, chloride, propylene glycol, propylene carbonate, glycofurol, cetyl alcohol, difluoroethane and isopropyl alcohol, preferably purified water. A selected pharmacological agent or mixture of two or more such agents in an appropriate amount from about 0.01 to about 3000 mg, is then dissolved in an aqueous or non-aqueous solvent, preferably a purified water. Both solutions are mixed together for from about 10 minutes to about several hours, preferably about 15-60 minutes, said mixture is spread over the flat surface or plate, such as a glass plate in a layer from 0.5 to about 2 mm, preferably about 1 mm, using, for example, a gel dryer, and let dry for as long as it takes for the water to completely evaporate. The film layer typically dries in about 24 to about 148 hours, usually in about 70 hours. Alternatively, the film may be prepared by spraying said mixture and drying.

In alternative embodiments, polymeric solutions with the drug and additives may be prepared in acetic acid, cyclohexane, acetonitrile, tert-butanol, ethanol, and isopropanol or in mixtures of aqueous and non-aqueous solvents.

1. Single Layer Films and Multiple-layer Films

Single-layer films containing drugs would be particularly useful applications where the film is in contact with tissue on both sides. Thus the drug would be able to diffuse out from both sides of the film.

Two-layer or more than two-layer films will be useful when a distinct function is required from the second layer.

For example, for buccal applications, a drug-eluting layer is most desirable against the mucous membrane. On the opposite side, however, a second barrier film layer may be useful to prevent loss of the drug into the saliva and the digestive system. Useful barrier film polymers include polyethylene terephthalate, polyethylene, and nylon.

As a functional example of a multi-layer film, a multi-layer film would consist of a barrier film as described above, a middle layer which serves as the primary reservoir for the drug, and a third layer comprising mucoadhesives and/or release modifiers, which contacts the body and controls the adhesion of the film to the tissue and the rate at which the drug is released from the reservoir layer.

4. Vaginal Sponge

Another example of the tampon-like device is the vaginal sponge. The mucosal composition comprising a desired therapeutical or health-enhancing agent can be incorporated into a silicone matrix which is coated onto a cylindrical drug-free polyurethane vaginal sponge.

A variation of the vaginal sponge is prepared in the same manner for buccal use.

5. Vaginal Ring

Another example of a vaginal device is the vaginal ring. Vaginal rings usually consist of an inert elastomer ring coated by another layer of elastomer containing the drug to be delivered. The rings can be easily inserted, left in place for the desired period of time, up to 7 days, then removed by the user. The ring may be solid or hollow containing the therapeutical and/or health-enhancing agent and it may be coated with an active layer material releasing the drug therefrom. The ring can optionally include a third, outer, rate-controlling elastomer inactive layer coating which contains no drug. Optionally, the third ring can also contain a second drug for a dual release ring. The drug can be incorporated into polyethylene glycol throughout the silicone elastomer ring to act as a reservoir for drug to be delivered.

6. Other Vaginal Devices

Vaginal pessaries, vaginal cylinders, vaginal tablets, vaginal capsules, vaginal pellets, vaginal pads, vaginal patches, vaginal suppositories or vaginal tubes are other examples of drug delivery systems which can be used in the present invention. These systems have been previously used for delivery of vaginal contraceptives, and have been described extensively in the literature.

These other types of vaginal devices are similarly coated on the side or on the end facing the uterus with the coating. For example the pessary or ring can be coated on the side facing the uterus with the other side remaining non-coated, sponge or pad may be coated at the portion closest to the uterus while the other side may be porous and adsorbent for, for example, the menstrual blood.

The vaginal device is provided in dry or wet form or may be wetted prior to insertion.

Variations of the vaginal devices described above are prepared in the same manner for buccal use.

B. Buccal Delivery

Buccal compositions, devices and delivery thereof are somehow similar in design, formulation and fabrication to those described for vaginal use. However, in contrast to vaginal formulations, in order not to interfere with physiological function of the mouth, buccal delivery systems are significantly smaller in size and more hydrophilic in nature. Consequently, Suppocire-based delivery systems described above for vaginal use are less appropriate for buccal delivery and incorporation into buccal devices, such as mucoadhesive foams, films and patches.

Transmucosal foams and films are particularly useful for buccal delivery of drugs as they permits transport of the drug into the systemic circulation directly through the mucosa, thereby avoiding invasive intravenous or less effective oral administration.

In one embodiment, this invention concerns buccal delivery systems that are designed to interact with the non-keratinized epithelium lining the oral cavity wherein drug released from these devices may act topically on the buccal mucosa or successfully traverse the barrier of the buccal epithelium and reach mucosa and submucosa areas where they gain access to the systemic circulation for distribution to targets distinctly separated from the site of administration.

Drug delivery via the buccal route is applicable to patients of both genders, achieves high compliance since it is non-invasive and offers easy access to the site of administration. The buccal mucosa is rich in blood vessels facilitating access to systemic circulation. Furthermore, drug absorbed from the buccal mucosa avoids hepatic first-pass metabolism similarly to the vaginal route.

A therapeutic composition, such as those described above, particularly foam or film compositions, according to the invention can be stand alone buccal devices or they may become a part of a more complex assembly comprising as one component the foam, film, cream, lotion, tablet, etc., and as a second component a device or formulation made of a different material. Such other device may be in the form of, for example, a structural device such as a strip, pad, sphere, pillow, tampon, tampon-like device, vaginal ring, sponge or pessary, or it may be in a form of a formulation, such as a tablet, paste, suppository, bioadhesive tablet, bioadhesive microparticles, cream, lotion, ointment, or gel.

The structural device such as the buccal pellet can be completely or partially coated or covered with the foam or film or the foam or film may be inserted inside of the device or into certain part of the device in any convenient arrangement.

In the alternative, the drug could be incorporated into the non-foam, non-film device, such as a pellet, and an empty foam or film composition could be used for coating or covering such device solely for the purpose of control of release rate.

These and other vaginal or buccal devices described in related patents and patent applications hereby incorporated by reference may be successfully utilized for delivery of anti-cancer or anti-viral drugs.

UTILITY

The current invention is useful for treatment of HIV/AIDS and cancer.

The bioavailability of drugs for the treatment of HIV/AIDS and cancer is markedly limited when the anti-cancer or antiviral drugs are administered by the oral route. This limitation is due to two specific related issues.

First, the absorption of the drugs is markedly limited due to the rapid expulsion of the drug from the gastrointestinal mucosa. Such expulsion is mediated by the intestinal efflux systems such as, for example, by P-glycoproteins, that affect and limit intestinal absorption of the drug leading to much lower concentrations of these drugs reaching the systemic circulation.

Second, there is extensive degradation of the drug presystemically in the gastrointestinal mucosa and, more predominantly, in the liver by a number of metabolizing enzymes. Chief among these enzymes are cytochrome P450 isozymes which are present in large concentrations in the intestinal mucosa and in the liver.

The oral administration of the drugs is further limited by the fact that almost all of them have major gastrointestinal toxicity which patients cannot tolerate especially with the administration of more than one of each agent in each class.

The current invention overcomes these problems by providing a method for vaginal/buccal drug delivery thereby eliminating problems encountered with the oral drug administration.

The invention is further applicable to other drugs having a low bioavailability, such as bisphosphonates, NSAIDS, anti-migraine and antiemetics drugs, antimicrobial or other drugs of this type.

EXAMPLE 1

Determination of Drug Class

To improve the efficiency of drug development and the review process by recommending a strategy for identifying expendable clinical bioequivalence tests, Biopharmaceutical Classification System (BCS) guidance was developed by the Office of Pharmaceutical Sciences.

The rationale for this system was to recommend a class of immediate-release (IR) solid oral dosage forms for which bioequivalence may be assessed based on in vitro dissolution tests, to recommend methods for classification according to dosage form dissolution, along with the solubility and permeability characteristics of the drug substance.

According to the BCS, drug substances are classified as follows:
Class I—High Permeability, High Solubility
Class II—High Permeability, Low Solubility
Class III—Low Permeability, High Solubility
Class IV—Low Permeability, Low Solubility A drug substance is considered highly soluble when the highest dose strength is soluble in $\leq 250$ ml water over a pH range of 1 to 7.5. Solubility is determined by pH-solubility profile of test drug in aqueous media with a pH range of 1 to 7.5.

A drug substance is considered highly permeable when the extent of absorption in humans is determined to be $\geq 90\%$ of an administered dose, based on mass-balance or in comparison to an intravenous reference dose. Permeability is determined by extent of absorption in humans, by mass-balance pharmacokinetic studies, by absolute bioavailability studies, by intestinal permeability methods, by in vivo intestinal perfusions studies in humans, by in vivo or in situ intestinal perfusion studies in animals, by in vitro permeation experiments with excised human or animal intestinal tissue, by in vitro permeation experiments across epithelial cell monolayers.

A drug product is considered to be rapidly dissolving when $\geq 85\%$ of the labeled amount of drug substance dissolves within 30 minutes using USP apparatus I or II in a volume of <900 ml buffer solutions. Dissolution is determined by using USP apparatus I (basket) at 100 rpm or USP apparatus II (paddle) at 50 rpm, by using a dissolution media (900 ml): 0.1 N HCl or simulated gastric fluid, pH 4.5 buffer, and pH 6.8 buffer or simulated intestinal fluid and by comparing dissolution profiles of test and reference products using a similarity factor ($f_2$).

EXAMPLE 2

Determination of Membrane Efflux Activity

This example describes experimental procedure that can be used for determination of differences in membrane efflux activity in the intestine, vagina or oral cavity mucosa.

Briefly, fresh mucosal samples are collected from female, white New Zealand rabbits, are separated from underlying connective tissue, and are mounted into modified Franz-type diffusion cells (5 mm diameter). Permeability studies from the apical to the basolateral as well as in the opposite direction are performed using continuous-flow perfusion chambers designed for mucosal tissue (Squier et al. *J. Pharm. Sci.*, 86, 82-84 (1997)). $^3$H-Ritonavir (~3 µCi/mL) dissolved in 1 mL of 0.01 M PBS, pH 7.4, is applied to the donor compartment, and the perfusate in the received compartment is collected into scintillation vials through 16 hrs. Radioactivity is determined by liquid scintillation counting using a Beckman LS 6500. Each transport experiment is performed in four replicate tissue samples. Apparent permeability coefficients ($P_{app}$) are calculated from steady state flux according to $P_{app}$ [cm/min]=($\Delta Q/\Delta t$)/Axc(0), where $\Delta Q/\Delta t$=linear appearance rate of mass in the receiver, A=cross-sectional area (i.e., 0.20 cm$^2$), and c(0)=initial ritonavir concentration in the donor compartment at t=0. Individual and mean $P_{app}$ values with corresponding standard deviations (S.D.) are calculated for each group. Statistical significance is tested by one-way analysis of variance (ANOVA) using Tukey's family error at p<0.05. To evaluate the contribution of membrane efflux system on ritonavir permeability $R_{efflux}$ was calculated as the ratio of $P_{app}$(basolateral-apical)/$P_{app}$(apical-basolateral).

EXAMPLE 3

Vaginal Paclitaxel Suppository

This example illustrates preparation of a vaginal suppository comprising paclitaxel.

To prepare 10 suppositories, 3.5 g of paclitaxel (Beijing Zhongshuo Pharmaceutical Technology Development Company, Ltd., Beijing, China) is dissolved in 11.5 mL of diethylene glycol monoethyl ether:isopropyl myristate:α-tocopherol (90:8:2, v/v) and supplemented with 115 mg of genistein. This drug-containing mixture is slowly added to 15.6 g of liquefied Suppocire® CM (Gattefossé, Paramus, N.J.) maintained at 50° C. Under vigorous stirring, 300 mg hydroxypropyl methylcellulose obtained as Methocel® K from Dow Chemical Company (Midland, Mich.) is added before the suspension is further cooled prior to packaging into PE/PVDC-coated PVC suppository sleeves.

The quantitative composition of vaginal paclitaxel suppositories is as follows: 350 mg of the anti-cancer agent paclitaxel (11.5%, w/w), 1560 mg of the lipophilic carrier Suppocire® CM (51.1%, w/w), 30 mg of the mucoadhesive agent hydroxypropyl methylcellulose (1.0%, w/w), 990 mg of the non-ionizable glycol ether diethylene glycol monoethyl ether (32.4%, w/w), 11.5 mg of the botanical bioavailability modulator genistein (0.4%, w/w), and 110 mg of additional excipients such as solubilizing agent and antioxidant (3.6%, w/w).

EXAMPLE 4

Vaginal Lopinavir Foam

This example illustrates a process for preparation of vaginal foam comprising lopinavir.

A 5% (w/w) polymeric mixture of sodium alginate (Sigma-Aldrich, Corp., St. Louis, Mo.) and hydroxypropyl methylcellulose obtained as Methocel® K from Dow Chemical Company (Midland, Mich.) is prepared at a 50:50 ratio in 0.5 M phosphate buffer, pH 7.8 heated between 70-85° C. This suspension is allowed to cool to approximately 45° C. before 350 mg of isobergapten (ChromaDex, Inc., Santa Ana, Calif.), 260 mg of naringenin (R&S Pharmchem Company, Ltd., Hangzhou City, China), and 1.86 g of the anti-viral drug lopinavir (Aquatic Remedis Pvt., Ltd., Mumbai, India) are dispersed in the cloudy mixture. Aliquots are filled into 10 mL syringes and allowed to cool before freezing the composition at –80° C. for at least 12 hours. The frozen cylindrical dose units are transferred to precooled metal trays and subjected to a freeze-drying process for at least 72 hours at –20° C. Following an additional 6 hours drying step at room temperature, vaginal lopinavir foams weighing each about 285 mg per 30 mm length are removed from the syringe and sealed in a moisture-impermeable pouch.

EXAMPLE 5

Vaginal Doxorubicin Film

This example illustrates preparation of vaginal film comprising doxorubicin.

A film precursor solution is prepared by mixing 14.0 mL of a polymer solution (4.1 g of water-soluble polyethylene oxide (MW ~200,000, 12-15 cPs/1% (w/v) solution at 25° C. and 0.9 g of Klucel® HF (Hercules, Inc., Wilmington, Del.) in 0.5 M phosphate buffer, pH 7.8 prepared in USP sterile water) with 6.0 mL of a doxorubicin solution prepared with 2.5 g of doxorubicin hydrochloride (Aquatic Remedis Pvt., Ltd., Mumbai, India), 350 mg of a Tween 20/Brij 30 mixture (45:55, v/v), 1.2 mL of diethylene glycol monoethyl ether, 500 mg of tangeretin, and 150 mg of sodium erythorbate in USP sterile water). Following low-speed centrifugation at 3000 rpm for 5 min, film precursor solution is placed into a rectangular area between two Sigmacote-treated glass plates separated by a 0.05 mm gap and dried to <3% (w/w) residual water using a gel-drying system (Hoefer Scientific Instruments, San Francisco, Calif.). Dried film layer is carefully peeled off from the glass plates and cut into rectangular units (1×3 inches) with an approximate weight between 200 to 250 mg.

EXAMPLE 6

Buccal Saquinavir Film

This example illustrates preparation of buccal saquinavir film.

The mesylate salt of the anti-viral drug saquinavir (5.2 g obtained from Aquatic Remedis Pvt., Ltd., Mumbai, India) is added to 5 mL of an aqueous solution of diethylene glycol monoethyl ether:Tween60:ethanol (35:10:32, v/v) that was supplemented with 25 mg and 15 mg of the antioxidants butylated hydroxylanisole and butylated hydroxytoluene, respectively. This drug suspension is combined with 10.5 mL of a polymer solution (300 mg of water-soluble polyethylene oxide (MW ~300,000, 20 cPs/1% (w/v) solution at 25° C., 1860 mg of Walocel®HM-6PA, and 465 mg of Walocel®HM-50PA (Bayer Corporation, West Heaven, Conn.) in USP sterile water. Following low-speed centrifugation at 3000 rpm for 5 min, film precursor mixture is placed into a rectangular area between two Sigmacote-treated glass plates separated by a 1 mm gap and dried to <3% (w/w) residual water using a gel-drying system (Hoefer Scientific Instruments, San Francisco, Calif.). Dried film layer is carefully peeled off from the glass plates and individual round 1 cm$^2$ dose units with an approximate weight between 200-250 mg are cut from the film sheets and laminated with an ethyl cellulose backing film.

What is claimed is:

1. An anti-viral or anti-cancer composition suitable for treatment of cancer and HIV/AIDS by providing a subject in need thereof with a mucosal composition administered vaginally or through an oral cavity, said composition comprising at least one anti-viral or one anti-cancer agent in an amount sufficient to provide a therapeutic effect in combination with 0.01 to 50% by weight of a non-ionizable glycol ether or with 0.001-10% by weight of a botanical bioavailability modulator, or a combination of both.

2. The composition of claim 1 wherein said anti-viral drug is an attachment inhibitor, fusion inhibitor, antiretroviral drug, nucleoside or nucleotide reverse transcriptase inhibitor or anti-HIV protease inhibitor.

3. The composition of claim 1 wherein said anti-cancer drug is an alkylating agent, antimetabolite, DNA cutter or DNA binder, topoisomerase I or topoisomerase II poison, or taxol or taxol derivative.

4. The composition of claim 1 wherein said non-ionizable glycol ether is selected from the group consisting of ethylene glycol monomethyl ether, diethylene glycol monomethyl ether, triethylene glycol monomethyl ether, polyethylene glycol monomethyl ether, ethylene glycol monoethyl ether, diethylene glycol monoethyl ether, triethylene glycol monoethyl ether, ethylene glycol monoisopropyl ether, ethylene glycol monobutyl ether, diethylene glycol monobutyl ether, triethylene glycol monobutyl ether, ethylene glycol monoisobutyl ether, diethylene glycol monohexyl ether, ethylene glycol mono 2-ethylhexyl ether, diethylene glycol mono 2-ethylhexyl ether, ethylene glycol monoallyl ether, ethylene glycol monophenyl ether, ethylene glycol monobenzyl ether, diethylene glycol monobenzyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, propylene glycol monophenyl ether, ethylene glycol dimethyl ether, diethylene glycol dimethyl ether, triethylene glycol dimethyl ether, diethylene glycol diethyl ether, diethylene glycol dibutyl ether, dipropylene glycol dimethyl ether, diethylene glycol monoethyl ether and ethoxydiglycol.

5. The composition of claim 1 wherein said botanical bioavailability modulator is selected from the group consisting of *Actaea racemosa* L. (Ranunculaceae), *Aesculus hippocastanum* L. (Hippocastanaceae), *Allium ampeloprasum* L. (Liliaceae), *Allium sativum* L. (Liliaceae), *Allium tuberosum* Rottl. (Liliaceae), *Alpinia galangal* L. (Zingiberaceae), *Boswellia carteri* Birdw. (Burseraceae), *Boswellia frereana* Birdw. (Burseraceae), *Boswellia sacra* Flueckiger (Burseraceae), *Boswellia serrata* Roxb. (Burseraceae), *Camelia sinensis* Kuntze (Theaceae), *Catharanthus roseus* L. (Apocyanaceae), *Cinnamomum burmani* Blume (Lauraceae), *Citrus aurantium* L. (Rutaceae), *Citrus paradisi* Macfad. (Rutaceae), *Crataegus oxyacantha* Rehd. (Rosaceae), *Curcuma longa* L. (Zingiberaceae), *Echinacea angustifolia* DC. (Asteraceae), *Echinacea pallida* Nutt. (Asteraceae), *Echinacea purpurea* Moench. (Asteraceae), *Eleutherococcus senticosus* Maxim. (Araliaceae), *Foeniculum vulgare* P. Mill. (Apiaceae), *Gingko biloba* L. (Ginkoaceae), *Glycine max* Merr. (Fabaceae), *Hydrastis Canadensis* L. (Ranunculaceae), *Hypericum perforatum* L. (Clausiaceae), *Hypoxis hemerocallidea* L. (Iridaceae), *Matricaria recutita* L., (Asteraceae), *Melaleuca leucadendra* L. (Myrtaceae), *Oenothera biennis* L. (Onagraceae), *Panax quinquefolius* L. (Araliaceae), *Piper methysticum* G. Forst. (Piperaceae), *Piper nigrum* L. (Piperaceae), *Salvia miltiorrhiza* L. (Lamiaceae), *Serenoa repens* Small (Arecaceae), *Serenoa serrulata* Nichols (Arecaceae), *Silybum marianum* Gaertn. (Asteraceae), *Strychnos ligustrina* Zipp. (Loganiaceae), *Sutherlandia frutescens* R. Br. (Fabaceae), *Tinospora crispa* Hook. f. & Thomson (Menispermaceae), *Uncaria tomentosa* Roxb. (Rubiaceae), *Valeriana officinalis* L. (Valerianaceae), *Vitis vinifera* L (Vitaceae), and *Zingiber cassumunar* Roxb. (Zingiberaceae), *Zingiber officinale* Roscoe (Zingiberaceae), and a constituent isolated from said modulator.

6. The method of claim 3 wherein said constituent is a purified or non-purified compound selected from the group consisting of actein, aescin, ajmalicine, allicin, berberine, bergamottin, bergapten, bilobalide, catechin, cimiracemosides A-F, cis-linoleic acid, curcumin, desmethoxyyangonin, dihydrokavain, dihydromethysticin, fatty acid ester, genistein, guar gum, ginkolic acid I and II, 3,3',4',5,6,7,8-heptamethoxyflavone, hydrastine, hyperforin, I3, II8-biapigenin, isobergapten, isorhemnetin, kaempferol, kavain, limonin, methysticin, naringenin, naringin, nobiletin, obacunone, oleanolic acid, pectin, piperine, quercetin, quinidine, S-allyl-L-cysteine, serpentine, silibinin, silichristin, silidianin, silybin, S-methyl-L-cysteine, sodium butyrate, tangeretin, taxifolin, ursolic acid, valerenic acid, vindoline, vintexin, 6,7-dihydroxybergamottin, and yangonin, said constituent incorporated into said composition in amount from about 0.01 to about 750 mg.

7. The composition of claim 1 wherein said composition further comprises a lipophilic carrier, a hydrophilic carrier, a mucoadhesive agent, a penetration enhancer, a sorption promoter, a solubilizing agent, antioxidant, buffer, plasticizer, lubricant, filler, stabilizer or emulsifier, alone or in combination.

8. The composition of claim 7 formulated as a suppository, gel, spray, film, foam, sponge, cream, tablet, capsule, emulsion, solution, lotion, suspension, particles, microparticles or bioadhesive microparticles.

9. The composition of claim 8 incorporated into, attached to, covering a vaginal device or a device insertable into an oral cavity, or is in contact with said device.

10. The composition of claim 9 wherein said vaginal device is a tampon, tampon-like device, ring, pessary, sponge, foam, tablet or pellet and wherein said device insertable into the oral cavity is a pellet, tablet, foam, film, pillow or strip.

11. The composition of claim 6 comprising the anti-viral agent darunavir, or the anti-cancer agent paclitaxel, each alone or in combination.

12. The composition of claim 11 administered vaginally or into an oral cavity in a therapeutically effective amount wherein said darunavir or paclitaxel is present in from about 0.001 to 3000 mg.

13. The composition of claim 12 formulated as a suppository, gel, spray, film, foam, sponge, cream, tablet, capsule, emulsion, solution, lotion, suspension, particles, microparticles or bioadhesive microparticles and administered vaginally or is incorporated into, attached to or covering a vaginal device, wherein said vaginal device is a tampon, tampon-like device, ring, pessary, sponge, foam, tablet or pellet.

14. The composition of claim 13 further comprising diethylene glycol monobutyl ester.

15. The composition of claim 14 further comprising a lipophilic carrier, a hydrophilic carrier, a mucoadhesive agent, a penetration enhancer, a sorpotion promoter, a solubilizing agent, antioxidant, buffer, plasticizer, lubricant, filler, stabilizer or emulsifier, alone or in combination.

16. The composition of claim 12 formulated as a gel, spray, film, foam, sponge, cream, tablet, capsule, emulsion, solution, lotion, suspension, particles, microparticles or bioadhesive microparticles and administered into an oral cavity or is incorporated into, attached to or covering a device insertable into the oral cavity, or is in contact with said device wherein said insertable device is a pellet, tablet, foam, film, pillow or strip.

17. The composition of claim 16 further comprising diethylene glycol monobutyl ester.

18. The composition of claim 17 wherein said composition further comprises a lipophilic carrier, a hydrophilic carrier, a mucoadhesive agent, a penetration enhancer, a sorption promoter, a solubilizing agent, antioxidant, buffer, plasticizer, lubricant, filler, stabilizer or emulsifier; alone or in combination.

19. The composition of claim 1 wherein said non-ionizable glycol ether is present in an amount of from 0.5 to 10%, by weight.

20. The composition of claim 8 wherein said at least one anti-viral or one anti-cancer agent is present in an amount from about 0.01 to about 3000 mg.

21. The composition of claim 1 wherein said anti-viral drug is selected from the group consisting of GSK-873, PRO-542, SCH-417690, TMC278, TNX-355, α-epibromide, Abacavir, Aldesleukin, Alovudine, Amdoxovir, Amprenavir, Capravirine, Cidifovir, Darunavir, Delavirdine, Dexelvucitabine, Didanosine, Elvucitabine, Emtricitabine, Enfuvirtide, Erythropeoietin, Etravirine, Fosamprenavir, Hydroxyurea, Indinavir, Lamivudine, Lopinavir, Maraviroc, Nelfinavir, Nevirapine, Ritonavir, Saquinavir, Somatropin, Stavudine, Tenofovir, Tipranavir, Zalcitabine, Zidovudine, AK602, AMD070, BMS-378806, INCB9471, Pro 140, SP01A, Vicriviroc, Gilead 9137, JTK-303, MK-0518, PA457, Panacos ADA, NSC 674447 and HGTV4.

22. The composition of claim 1 wherein said anti-cancer agent is selected from the group consisting of Amsacrine, Bleomycin, Busulfan, Capecitabine, Carboplatin, Carmustine, Chlorambucil, Cisplatin, Cladribine, Crisantaspase, Cyclophosphamide, Cytarabine, Dacarbazine, Dactinomycin, Daunorubicin, Docetaxel, Doxorubicin, Epirubicin, Etoposide, Floxuridine, Fludarabine, Fluorouracil, Gemcitabine, Idarubicin, Ifosfamide, Irinotecan, Leucovorin, Lomustine, Melphalan, Mercaptopurine, Mesna, Methotrexate, Mitomycin, Mitoxantrone, Oxaliplatin, Paclitaxel, Pemetrexed, Pentostatin, Procarbazine, Raltitrexed, Streptozocin, Temozolomide, Teniposide, Thiotepa, Thioguanine, Topotecan, Trimetrexate, Vinblastine, Vincristine, Vindesine, Vinorelbine, Mechlorethamine, Ara-CMP, and Camptothecin.

* * * * *